(12) United States Patent
McIntosh et al.

(10) Patent No.: US 6,328,960 B1
(45) Date of Patent: Dec. 11, 2001

(54) MESENCHYMAL STEM CELLS FOR PREVENTION AND TREATMENT OF IMMUNE RESPONSES IN TRANSPLANTATION

(75) Inventors: Kevin R. McIntosh; Joseph D. Mosca, both of Ellicott City; Elena N. Klyushnenkova, Baltimore, all of MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/267,536

(22) Filed: Mar. 12, 1999

Related U.S. Application Data

(60) Provisional application No. 60/078,463, filed on Mar. 18, 1998, and provisional application No. 60/089,964, filed on Jun. 19, 1998.

(51) Int. Cl.[7] .......................... A01N 63/00; A61K 35/14; A61K 35/28; C12Q 1/12
(52) U.S. Cl. ................ 424/93.71; 424/529; 424/577; 435/1.1; 435/37.2
(58) Field of Search ................ 435/1.1, 372; 424/93.71, 424/529, 577

(56) References Cited

U.S. PATENT DOCUMENTS 5,733,542   3/1998   Haynesworth et al. ............ 424/93.7

OTHER PUBLICATIONS

Anderson, W. F. Human gene therapy. Nature 392:25–30, 1998.*

Hojo, et al., "cyclosporine induces cancer progression by a cell–autonomous mechanism," *Nature*, 397:530–534 (1999).

* cited by examiner

*Primary Examiner*—David Saunders
*Assistant Examiner*—Mary Beth Tung
(74) *Attorney, Agent, or Firm*—Elliot M. Olstein; Alan J. Grant

(57) ABSTRACT

Disclosed is a method of reducing an immune response to a transplant in a recipient by treating said recipient with an amount of mesenchymal stem cells effective to reduce or inhibit host rejection of the transplant. The mesenchymal stem cells can be administered before, at the same time as, or after the transplant. Also disclosed is a method of inducing a reduced immune response against a host by foreign tissue, i.e., graft versus host disease, by treatment with mesenchymal stem cells.

22 Claims, 10 Drawing Sheets

Stimulator: E645 PBMC

Stimulator: E647 PBMC

MESENCHYMAL STEM CELLS FOR PREVENTION AND TREATMENT OF IMMUNE RESPONSES IN TRANSPLANTATION

This application is based on and claims priority of U.S. provisional application Ser. No. 60/078,463 filed Mar. 18, 1998 and U.S. provisional application Ser. No. 60/089,964 filed Jun. 19, 1998.

The present invention relates to inhibiting a T cell response to an alloantigen and further relates to inhibiting and/or preventing reactivation of previously activated T cells. More particularly, the present invention relates to the field of preventing, reducing or treating an immune response caused by immune effector cells to foreign tissue and/or cells and/or organs. The invention further relates to preventing, reducing or treating transplant rejection and/or graft versus host reaction.

BACKGROUND OF THE INVENTION

Tolerance is the acquired lack of specific responsiveness to an antigen to which an immune response would normally occur. Typically, to induce tolerance, there must be an exposure to a tolerizing antigen, which results in the death or functional inactivation of certain lymphocytes. Complete tolerance is characterized by the lack of a detectable immune response, either antibody or cell mediated, to the second antigenic challenge. Partial tolerance is typified by the quantitative reduction of an immune response.

The function of the immune system is to eliminate foreign bodies which may contain pathogens, and to maintain unresponsiveness or tolerance against self antigen. T cell tolerance is achieved 1) in the thymus where thymocytes reactive for self-peptides are eliminated by clonal deletion (central tolerance), and 2) in the periphery by exposure to self-antigens under tolerogenic conditions (peripheral tolerance). Clonal deletion can also result from expression of cell death molecules on antigen presenting cells. Classic examples of death molecules are Fas ligand (FasL) and TRAIL ligand, which ligate their receptors, Fas and DR4, respectively, on activated T cells, inducing apoptosis of the T cells. The interaction of CD27, a member of the TNFR superfamily, and the CD27-ligand (CD70) also induces T cell apoptosis.

Unfortunately, the immune system does not distinguish beneficial intruders, such as transplanted tissue, from those that are harmful, and thus the immune system rejects transplanted tissue or organs. Rejection of transplanted organs is significantly mediated by alloreactive T cells present in the host which recognize donor alloantigens or xenoantigens.

At present, in order to prevent or reduce an immune response against a transplant, patients are treated with powerful immunosuppressive drugs. The infusion of individuals with drugs that prevent or suppress T-cell immune response does inhibit transplant rejection, but can also result in general immune suppression, toxicity and even death due to opportunistic infections. Because of the toxicity and incomplete response rate to conventional treatment of donor tissue rejection, alternative approaches are needed to treat patients who cannot withstand or do not respond to current modes of drug therapy.

Accordingly, there is a need for the prevention and/or reduction of an unwanted immune response by a host to a transplant by immune effector cells as a method to avert host rejection of donor tissue. Also advantageous would be a method to eliminate or reduce an unwanted immune response by a donor tissue against a recipient tissue, known as graft-versus-host disease.

SUMMARY OF THE INVENTION

It has been discovered that human mesenchymal stem cells can be used in transplantation to ameliorate a response by the immune system such that an immune response to an antigen(s) will be reduced or eliminated.

In accordance with one aspect of the invention, there is provided a method for reducing or suppressing an immune response caused by T cells responding to an alloantigen, in particular allogeneic tissue, organ or cells, wherein the immune response is reduced or suppressed by the use of mesenchymal stem cells. The mesenchymal stem cells may be autologous to the T cells (obtained from the same host) or allogeneic to the T cells. In the case of mesenchymal stem cells that are allogeneic to the T cells, the mesenchymal stem cells may be autologous to the cells or tissue to which the T cells are responding (obtained from the same host) or the mesenchymal stem cells may be obtained from a host that is allogeneic to both the source of the T cells and the source of the cells or tissue to which the T cells are responding.

In accordance with another aspect of the present invention there is provided a process for preventing restimulation of activated T cells (activated against an alloantigen, in particular an allogeneic organ, tissue or cells) by contacting activated T cells with mesenchymal stem cells in an amount effective to prevent and/or reduce a subsequent T cell response to a foreign antigen. The mesenchymal stem cells that are used may be autologous to the T cells and/or allogeneic to the T cells. When using allogeneic mesenchymal stem cells, the mesenchymal stem cells may be obtained from the same host as the tissue or cells that activated the T cells or may be obtained from a host that is allogeneic to both the T cells and the host that provided the cells or tissues that activated the T cells.

In accordance with another aspect of the present invention, mesenchymal stem cells are used to suppress or ameliorate an immune response to a transplant (tissue, organ, cells, etc.) by administering to the transplant recipient mesenchymal stem cells in an amount effective to suppress or ameliorate an immune response against the transplant. The mesenchymal stem cells may be autologous to the transplant recipient or may be allogeneic to the transplant recipient.

Accordingly, one method of the present invention provides contacting the recipient of donor tissue with mesenchymal stem cells. In one embodiment of this aspect, the method involves administering mesenchymal stem cells to the recipient of donor tissue. The mesenchymal stem cells can be administered to the recipient before or at the same time as the transplant or subsequent to the transplant. The mesenchymal stem cells may be autologous or may be allogeneic to the recipient and can be obtained from the donor. In another aspect of the invention, the allogeneic mesenchymal stem cells can also be obtained from a source other than the donor and such source need not be matched either to the donor type or the recipient type.

In a further embodiment of this method, as part of a transplantation procedure the mesenchymal stem cells are modified to express a molecule that induces cell death. The mesenchymal stem cells can be used to deliver to the immune system a molecule that induces apoptosis of activated T cells carrying a receptor for the molecule. This results in the deletion of activated T lymphocytes and in the suppression of an unwanted immune response to a transplant. In accordance with this aspect of the invention, allogeneic human mesenchymal stem cells are modified to express a cell death molecule. The molecule can be exogenous or endogenous to the mesenchymal stem cells. In preferred embodiments of the methods described herein, the mesenchymal stem cells express the cell death molecule Fas ligand or TRAIL ligand.

The mesenchymal stem cells can also be administered to the recipient as part of the transplant. To this objective, the present invention provides a method for reducing or ameliorating an immune response by providing to the recipient donor tissue or organ that is perfused with or includes mesenchymal stem cells obtained from the donor of the organ or tissue or mesenchymal stem cells from a third party or mesenchymal stem cells autologous to the T cells. The mesenchymal stem cells ameliorate an immune response by the recipient's T cells against the foreign tissue when it is transplanted into the recipient.

In a further embodiment of this invention, the mesenchymal stem cells perfused into the organ or tissue also can include a molecule that induces activated T cell death.

In another embodiment, the method of the present invention provides treating a patient who has received a transplant, in order to reduce the severity of or eliminate a rejection episode against the transplant, by administering to the recipient of donor tissue mesenchymal stem cells after the donor tissue has been transplanted into the recipient. The mesenchymal stem cells can be autologous or allogeneic to the recipient. The allogeneic mesenchymal stem cells can be obtained from the donor or from a third party source. The presentation of mesenchymal stem cells to a recipient undergoing an adverse immune response to a transplant induces nonresponsiveness of T cells to further antigenic stimulation thereby reducing or eliminating an adverse response by activated T cells to donor tissue or organ.

In a further aspect of the present invention, there is provided a method of reducing an immune response by donor tissue, organ or cells against a recipient, i.e. graft versus host response, comprising treating the donor tissue, organ or cells with allogeneic (allogeneic to the donor) mesenchymal stem cells ex vivo prior to transplantation of the tissue, organ or cells into the recipient. The mesenchymal stem cells reduce the responsiveness of T cells in the transplant that may be subsequently activated against recipient antigen presenting cells such that the transplant may be introduced into the recipient's (host's) body without the occurrence of, or with a reduction in, an adverse response of the transplant to the host. Thus, what is known as "graft versus host" disease may be averted.

In a preferred embodiment, the donor transplant may be first exposed to recipient or third party tissue or cells ex vivo, to activate the T cells in the donor transplant. The donor transplant is then contacted with mesenchymal stem cells autologous or allogeneic to the donor. The mesenchymal stem cells can be recipient or third party mesenchymal stem cells. The mesenchymal stem cells will reduce or inhibit an adverse secondary immune response by T cells in the donor transplant against antigenic stimulation by the recipient when the donor transplant is subsequently placed into the recipient.

Accordingly, the mesenchymal stem cells can be obtained from the recipient, for example, prior to the transplant. The mesenchymal stem cells can be isolated and stored frozen until needed. The mesenchymal stem cells may also be culture-expanded to desired amounts and stored until needed. The mesenchymal stem cells are administered to the recipient in an amount effective to reduce or eliminate an ongoing adverse immune response caused by the donor transplant against the recipient (host). The presentation of the mesenchymal stem cells to the recipient undergoing an adverse immune response caused by a transplant inhibits the ongoing response and prevents restimulation of the T cells thereby reducing or eliminating an adverse response by activated T cells to recipient tissue.

A further embodiment includes modifying the recipient's mesenchymal stem cells with a molecule that induces activated T cell death.

Thus, in accordance with preferred embodiments of the present invention, human mesenchymal stem cells are employed to treat transplant rejection and or graft versus host disease as a result of a transplant and or to prevent or reduce transplant rejection and or graft versus host disease. Human mesenchymal stem cells may also be employed to facilitate the use of xenogeneic grafts or transplants.

DETAILED DESCRIPTION OF THE INVENTION

Figure 1:
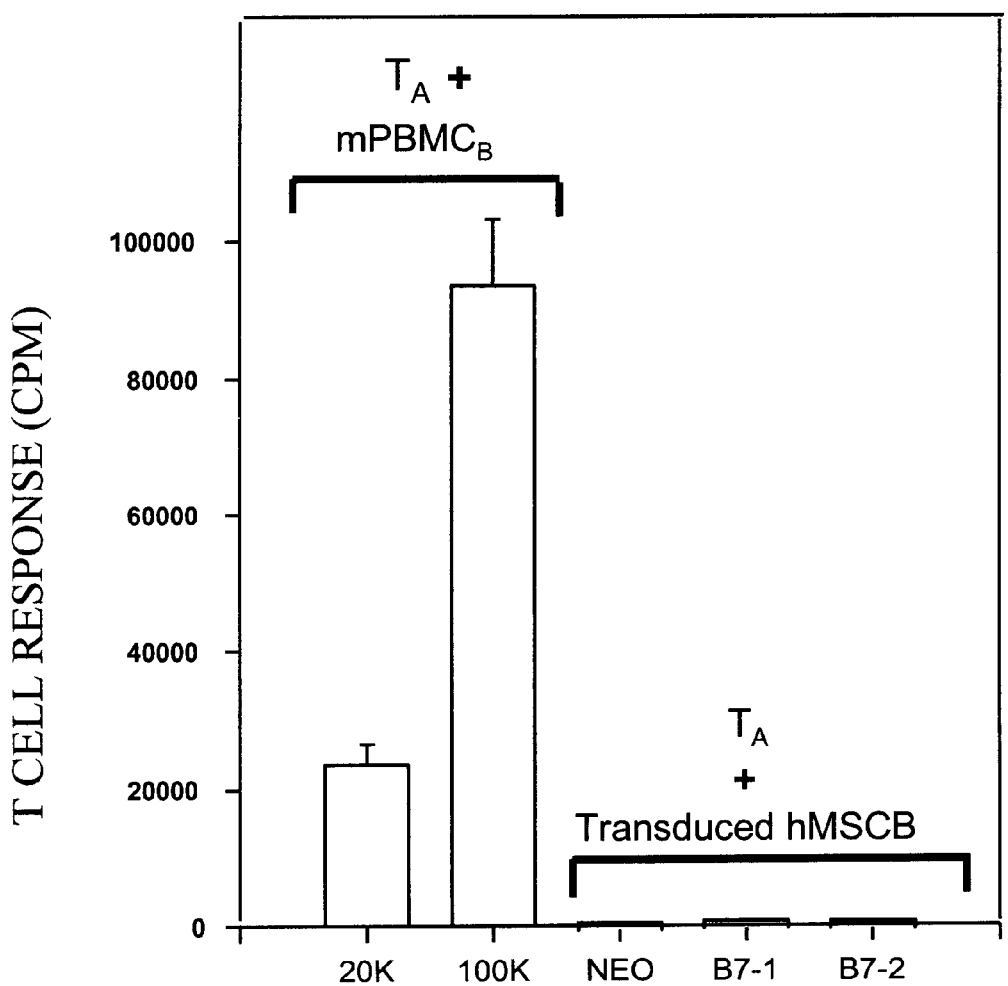
FIG. 1 Allogeneic mesenchymal stem cells do not induce an immune response. T cells from A proliferated in a dose dependent manner when mixed with different amounts of PBMCs from B. T cells from A did not proliferate in response to contact with mesenchymal stem cells from B, even when the mesenchymal stem cells were manipulated to provide full T cell activation (the mesenchymal stem cells were treated with IFN-γ and transduced with costimulatory molecules B7-1 or B7-2).

As defined herein, an allogeneic mesenchymal stem cell is obtained from a different individual of the same species as the recipient. Donor antigen refers to antigens expressed by the donor tissue to be transplanted into the recipient. Alloantigens are antigens which differ from antigens expressed by the recipient. Donor tissue, organs or cells to be transplanted is the transplant. As examples of transplants may be included skin, bone marrow, and solid organs such as heart, pancreas, kidney, lung and liver.

The inventors have discovered that when human mesenchymal stem cells are contacted with allogeneic T lymphocytes, in vitro, the allogeneic T cells do not proliferate. Normally, co-culturing cells from different individuals results in a T cell response, manifested by activation and proliferation of the T cells, known as a mixed lymphocyte reaction (MLR).

These unexpected results demonstrate that T cells are not responsive to mismatched mesenchymal stem cells. The lack of a proliferative response to human mesenchymal stem cells by allogeneic T cells was unexpected because human mesenchymal stem cells express surface molecules that should render them immunogenic, i.e., they express allogeneic class I MHC molecules. This discovery indicates that the mesenchymal stem cells are not immunogenic to the immune system.

The inventors also discovered that mesenchymal stem cells can suppress an MLR between allogeneic cells. Mesenchymal stem cells actively reduced the allogeneic T cell response in mixed lymphocyte reactions in a dose dependent manner. In addition, mesenchymal stem cells from different donors did not exhibit specificity of reduced response with regard to MHC type. Thus, mesenchymal stem cells did not need to be MHC matched to the target cell population in the mixed lymphocyte reaction in order to reduce the proliferative response of alloreactive T cells to mesenchymal stem cells.

Accordingly, the present invention provides a method of reducing, inhibiting or eliminating an immune response by administering allogeneic mesenchymal stem cells to a recipient of a donor tissue, organ or cells. In one embodiment, the mesenchymal stem cells are administered to the recipient contemporaneously with the transplant. Alternatively, the human mesenchymal stem cells can be administered prior to the administration of the transplant. For example, the human mesenchymal stem cells can be administered to the recipient about 3 to 7 days before transplantation of the donor tissue.

Thus, mesenchymal stem cells can be used to condition a recipient's immune system to donor or foreign tissue by administering to the recipient, prior to, or at the same time as transplantation of the donor tissue, mesenchymal stem cells in an amount effective to reduce or eliminate an immune response against the transplant by the recipient's T cells. The mesenchymal stem cells affect the T cells of the recipient such that the T cell response is reduced or eliminated when presented with donor or foreign tissue. Thus, host rejection of the transplant may be avoided or the severity thereof reduced.

The inventors have further discovered that when T lymphocytes that have already been exposed to antigenic stimulation, i.e. are activated, are subsequently exposed to mesenchymal stem cells, the T cells do not produce or produce a reduced immune response to subsequent antigenic stimulation by allogeneic cells. Thus, mesenchymal stem cells induce a state of hyporesponsiveness of the T cells.

These unexpected results demonstrate that activated T cells were made non-responsive to further allogeneic stimulation by exposure of preactivated T cells to human mesenchymal stem cells. The mesenchymal stem cells can be autologous or allogeneic to the T cells.

Accordingly, the present invention provides a method for treating a patient who is undergoing an adverse immune response to a transplant by administering mesenchymal stem cells to such patient in an amount effective to reduce or suppress the immune response. The mesenchymal stem cells are obtained from the tissue donor, the transplant recipient or a third party.

The mesenchymal stem cells may further be modified to express a cell death molecule to enhance the elimination of activated T cells. For example, the cell death molecule may be expressed by the mesenchymal stem cells which have been engineered to express the exogenous cell death molecule.

In another aspect, the present invention provides a method to reduce or inhibit or eliminate an immune response by a donor transplant against a recipient thereof (graft versus host). Accordingly, the invention provides contacting a donor organ or tissue with mesenchymal stem cells prior to transplant. The mesenchymal stem cells ameliorate, inhibit or reduce an adverse response by the donor transplant against the recipient.

In a preferred embodiment, prior to transplant the donor transplant is treated with allogeneic (recipient) tissue or cells which activate the T cells in the donor transplant. The donor transplant is then treated with mesenchymal stem cells, autologous or allogeneic, prior to transplant. The mesenchymal stem cells prevent restimulation, or induce hyporesponsiveness, of the T cells to subsequent antigenic stimulation.

For preconditioning a donor transplant, the mesenchymal stem cells may be further modified to express a cell death molecule such that activated T cells contacted with the mesenchymal stem cells will be eliminated.

Thus, in the context of bone marrow (hematopoietic stem cell) transplantation, attack of the host by the graft can be reduced or eliminated. Donor marrow can be pretreated with recipient mesenchymal stem cells prior to implant of the bone marrow or peripheral blood stem cells into the recipient. In a preferred embodiment, the donor marrow is first exposed to recipient tissue/cells and then treated with mesenchymal stem cells. Although not being limited thereto, it is believed that the initial contact with recipient tissue or cells functions to activate the T cells in the marrow. Subsequent treatment with the mesenchymal stem cells inhibits or eliminates further activation of the T cells in the marrow, thereby reducing or eliminating an adverse affect by the donor tissue, i.e. the therapy reduces or eliminates graft versus host response.

In a further embodiment, a transplant recipient suffering from graft versus host disease may be treated to reduce or eliminate the severity thereof by administering to such recipient mesenchymal stem cells autologous or allogeneic to the donor, which allogeneic cells can be mesenchymal stem cells autologous to the recipient or third party mesenchymal stem cells, in an amount effective to reduce or eliminate a graft rejection of the host. The mesenchymal stem cells inhibit or suppress the activated T cells in the donor tissue from mounting an immune response against the recipient, thereby reducing or eliminating a graft versus host response.

The recipient's mesenchymal stem cells may be obtained from the recipient prior to the transplantation and may be stored and/or culture-expanded to provide a reserve of mesenchymal stem cells in sufficient amounts for treating an ongoing graft attack against host.

In yet another method of the present invention, the donor tissue is exposed to mesenchymal stem cells such that the mesenchymal stem cells integrate into the organ graft itself prior to transplantation. In this situation, an immune response against the graft caused by any alloreactive recipient cells that escaped standard treatment to prevent transplant rejection, e.g., drug-mediated immunosuppression, would be suppressed by the mesenchymal stem cells present in the graft. The mesenchymal stem cells are preferably allogeneic to the recipient and may be donor mesenchymal stem cells or mesenchymal stem cells obtained from other than the donor or recipient. In some cases, mesenchymal stem cells autologous to the recipient may be used to suppress an immune response against the graft.

In a further embodiment of this method, the mesenchymal stem cells are engineered to express cell death molecules such that any alloreactive host T cells will be eliminated upon contact with these mesenchymal stem cells.

It is further believed that in addition to preventing or ameliorating an initial immune response, the mesenchymal stem cells remaining in the local site would also suppress any subsequent T cell response that may occur.

As used herein, a "cell death molecule" is a molecule that interacts or binds with its cognate receptor on a stimulated T cell inducing T cell death or apoptosis. Fas mediates apoptosis of recently activated T cells which are again exposed to stimulation (van Parijs et al., *Immunity* 4: 321–328 (1996)). Fas is a type I membrane receptor that when crosslinked by its cognate ligand induces apoptosis in a wide variety of cells. The interaction between the Fas molecule (CD95) on target T cells and its ligand Fas L on mesenchymal stem cells results in receptor aggregation, which transduces signals leading to apoptosis of the target cell. The Fas system has been shown to be involved in a number of cell functions in vivo including negative selection of thymocytes, maintaining immune privilege sites within the body, and cytotoxic T-lymphocyte (CTL)-mediated cytotoxicity (Green and Ware, *Proc Natl Acad Sci*, 94(12): 5986–90 (1997)).

Other members of the tumor necrosis factor receptor (TNFR) family have roles in programmed cell death. TRAIL ligand, which interacts with its receptor DR4 can induce apoptosis in a variety of transformed cell lines (G. Pan et al. *Science*, 277:815–818 (1997)); and the expression of CD27 and its ligand CD70 (Prasad et al., Proc Natl Acad Sci, 94:6346-6351 (1997)) also induces apoptosis. Fas expression is restricted to stimulated T cells and sites of immune privilege. TRAIL is detected in many normal tissues.

Both Trail-ligand and CD27, but not Fas-ligand, are expressed on unmanipulated human mesenchymal stem cells. Activated, but not resting, T cells express the Trail receptor and CD70. Most of the T cells found in the body are in the resting state; T cells are activated when they encounter cells both in the context of MHC and the appropriate co-stimulatory molecule such as B7-1 or B7-2.

Thus, the engagement of cell death receptors on activated T cells with their ligands expressed on the mesenchymal stem cells results in T cell death via apoptosis. Ligands and their receptors other than those specifically mentioned above, either present within the mesenchymal stem cell or introduced into the mesenchymal stem cell can perform this function. Therefore, mesenchymal stem cells administered to an individual delete activated T cells, reducing the severity or incidence of transplant rejection disease.

In accordance with the methods of the present invention described herein, it is contemplated that the mesenchymal stem cells of the present invention can be used in conjunction with current modes of treating donor tissue rejection or graft versus host disease. An advantage of such use is that by ameliorating the severity of the immune response in a transplant recipient, the amount of drug used in treatment and/or the frequency of administration of drug therapy can be reduced, resulting in alleviation of general immune suppression and unwanted side effects.

It is further contemplated that only a single treatment with the mesenchymal stem cells of the present invention may be required, eliminating the need for chronic immunosuppressive drug therapy. Alternatively, multiple administrations of mesenchymal stem cells may be employed.

Accordingly, the invention described herein provides for preventing or treating transplant rejection by administering the mesenchymal stem cells in a prophylactic or therapeutically effective amount for the prevention or treatment or amelioration of transplant rejection of an organ, tissue or cells from the same species, or a xenograft organ or tissue transplant and or graft versus host disease.

Administration of a single dose of mesenchymal stem cells may be effective to reduce or eliminate the T cell response to tissue allogeneic to the T cells or to "non-self" tissue, particularly in the case where the T lymphocytes retain their nonresponsive character (i.e., tolerance or anergy) to allogeneic cells after being separated from the mesenchymal stem cells.

The dosage of the mesenchymal stem cells varies within wide limits and will, of course be fitted to the individual requirements in each particular case. In general, in the case of parenteral administration, it is customary to administer from about 0.01 to about 5 million cells per kilogram of recipient body weight. The number of cells used will depend on the weight and condition of the recipient, the number of or frequency of administrations, and other variables known to those of skill in the art. The mesenchymal stem cells can be administered by a route which is suitable for the tissue, organ or cells to be transplanted. They can be administered systemically, i.e., parenterally, by intravenous injection or can be targeted to a particular tissue or organ, such as bone marrow. The human mesenchymal stem cells can be administered via a subcutaneous implantation of cells or by injection of stem cell into connective tissue, for example muscle.

The cells can be suspended in an appropriate diluent, at a concentration of from about 0.01 to about $5 \times 10^6$ cells/ml. Suitable excipients for injection solutions are those that are biologically and physiologically compatible with the cells and with the recipient, such as buffered saline solution or other suitable excipients. The composition for administration must be formulated, produced and stored according to standard methods complying with proper sterility and stability.

Although the invention is not limited thereof, mesenchymal stem cells can be isolated, preferably from bone marrow, purified, and expanded in culture, i.e. in vitro, to obtain sufficient numbers of cells for use in the methods described herein. Mesenchymal stem cells, the formative pluripotent blast cells found in the bone, are normally present at very low frequencies in bone marrow (1:100,000) and other mesenchymal tissues. See, Caplan and Haynesworth, U.S. Pat. No. 5,486,359. Gene transduction of mesenchymal stem cells is disclosed in Gerson et al U.S. Pat. No. 5,591,625.

Unless otherwise stated, genetic manipulations are performed as described in Sambrook and Maniatis, MOLECULAR CLONING: A LABORATORY MANUAL, 2nd Ed.; Cold Spring Harbor Laboratory Press, Cold Spring Harbor, N.Y. (1989).

It should be understood that the methods described herein may be carried out in a number of ways and with various modifications and permutations thereof that are well known in the art. It may also be appreciated that any theories set forth as to modes of action or interactions between cell types should not be construed as limiting this invention in any manner, but are presented such that the methods of the invention can be more fully understood.

The following examples further illustrate aspects of the present invention. However, they are in no way a limitation of the teachings or disclosure of the present invention as set forth herein.

EXAMPLE 1

Absence of Alloreactivity of Mesenchymal Stem Cells

The mixed lymphocyte reaction measures the compatibility of the donor's surface antigens and is an indication of the likelihood of rejection of donor tissue. Cell surface antigens responsible for eliciting transplant rejection are class I and class II MHC antigens. T cells are alloreactive to foreign MHC antigens. Class I and II MHC molecules stimulate the mixed lymphocyte reaction.

Normal human volunteers were leukopheresed on a COBE SPECTRA™ apheresis system (COBE, Lakewood, Co.). $1\times10^5$ T cells from individual A ($T_A$) were cultured in flat bottom microtiter wells with mitomycin C treated allogeneic PBMCs (to prevent proliferation of PBMCs to T cells) from individual B (m$PBMC_B$) for 7 days. The mPB-$MC_B$s were seeded at 20K and 100K. The cultures were pulsed with $^3$H-thymidine for the last 18 hours of the culture period to measure T cell proliferation. The results shown in FIG. 1 indicate that the $T_A$ cells recognized the $PBMC_B$ as being foreign. (See bars under "$T_A$+m$PBMC_B$".) With more $PBMC_B$s present, the more the T cells proliferated.

$2\times10^4$ human mesenchymal stem cells (hMSCs) from the same donor as the PBMCs were co-incubated with $1\times10^5$ T cells from individual A ($T_A$). The cells were cultured in flat-bottom microtiter wells for a total of 7 days. Cultures were pulsed with $^3$H-thymidine for the last 18 hours of the culture period to measure T cell proliferation. Two days prior to coculture with the T cells, the human mesenchymal stem cells were seeded into microtiter wells at the number given above (confluent) and treated with IFN-γ (50 units/ml) to stimulate surface antigen expression on MSCs. Non-transduced hMSCs or hMSCs transduced with human B7-1 or human B7-2 costimulation molecules were incubated with the T cells. Control cells were transduced with Neo.

The results shown in FIG. 1 (See FIG. 1 "$T_A$+transduced hMSCs") demonstrate that the T lymphocytes were nonresponsive (did not proliferate) to the human mesenchymal stem cells, i.e., they were not recognized as being foreign.

The results also show that the lack of response to the mesenchymal stem cells was not due to genetic compatibility between the individuals since the T cells did recognize peripheral blood mononuclear cells ($PBMC_B$) from the hMSC donor as being foreign.

EXAMPLE 2

Suppression of Mixed Lymphocyte Reaction

To determine whether mesenchymal stem cells actively suppressed the allogeneic response, mixed lymphocyte reactions (MLR) were set up in tissue culture plates, with or without adherent mesenchymal stem cells obtained from 2 different donors: one donor matched the stimulator cells in the MLR and the other donor was unrelated to either the stimulator or responder cells.

$10^5$ PBMCs from individual A ($PBMC_A$) were mixed with $10^5$ target individual B's PBMC's ($PBMC_B$). The $PBM_B$s were irradiated with 3000 rads X irradiation to prevent their proliferation due to activation by $PBMC_A$S. Thus, only $PBMC_A$s would proliferate. When $PBMC_A$s and $PBMC_B$s were mixed, a mixed lymphocyte reaction occurred wherein the $PBMC_A$ cells (responder cells) were activated by the surface antigens on the $PBMC_B$s (stimulator cells). The cultures were incubated over an interval of 7 days and were pulsed with $^3$H-thymidine during the final 18 hours. In the presence of the $PBMC_B$s, the $PBMC_A$S proliferated giving counts of 40,000. See FIG. 2, 1st bar, ("NONE" refers to no mesenchymal stem cells present.).

However, when $PBMC_A$s and $PBMC_B$s were mixed in the presence of mesenchymal stem cells, the mixed lymphocyte reaction was suppressed. $10^5$ $PBMC_A$s were mixed with $10^5$ $PBMC_B$s in microtiter plate wells coated with an adherent monolayer of human mesenchymal stem cells. The mesenchymal stem cells were plated in the wells in amounts ranging from 7500 to 22,500 mesenchymal stem cells per well. Two mesenchymal stem cell populations were tested: human mesenchymal stem cells were obtained from an individual B and human mesenchymal stem cells were obtained from an individual that did not match either individual A's or B's MHC type (a third party). The cultures were incubated over an interval of 7 days and were pulsed with $^3$H-thymidine during the final 18 hours. In the presence of the human mesenchymal stem cells, the MLR was suppressed. See FIG. 2. Thus, regardless of the MHC origin of the mesenchymal stem cells, the mesenchymal stem cells suppressed the mixed lymphocyte reaction.

Figure 2:
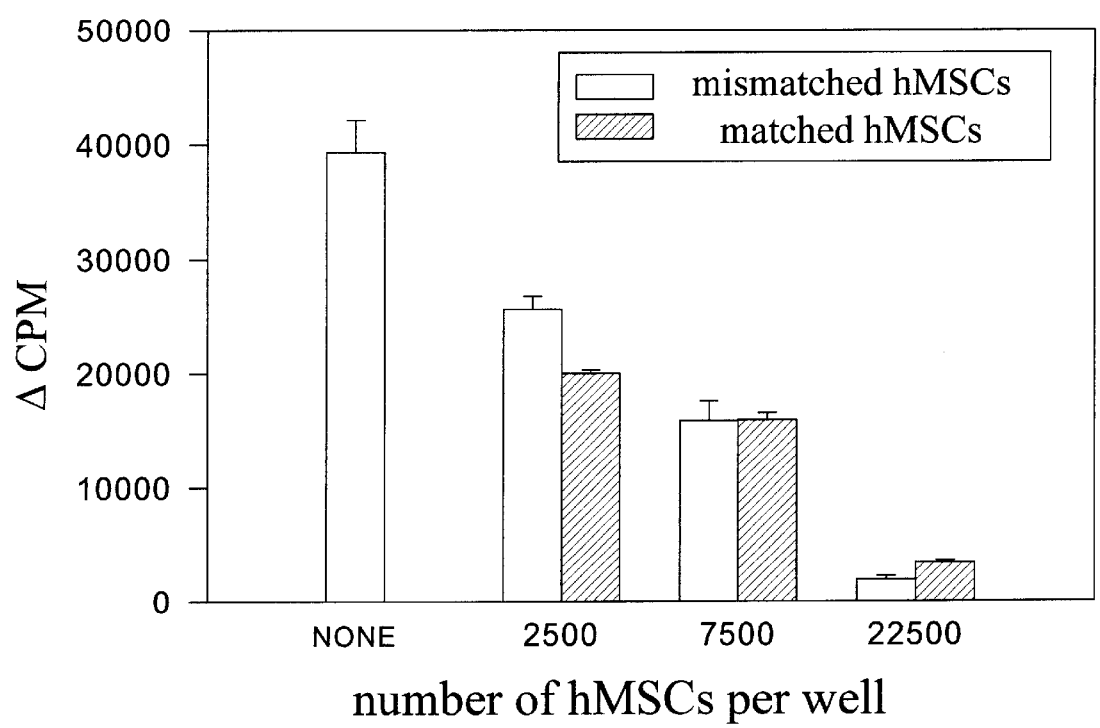
FIG. 2 Mesenchymal stem cells actively suppressed the mixed lymphocyte reaction (MLR) between lymphocytes from two different individuals. hMSCs allogeneic to recipient (third party or donor) were either mismatched to both the stimulator and responder cells in the (MLR) (open bars); or hMSCs were matched (donor) to the stimulator cells in the MLR (hatched bars). Thus, the mesenchymal stem cells suppressed the MLR without specificity as to MHC type. The mesenchymal stem cells suppressed the MLR in a dose dependent manner.

The results shown in FIG. 2 also indicate that the human mesenchymal stem cells decreased the mixed lymphocyte reaction in a dose-dependent manner. Mesenchymal stem cells from either donor suppressed proliferation equally well, which indicated that there was no specificity of suppression with respect to MHC type. These results demonstrate that mesenchymal stem cells actively suppressed the mixed lymphocyte reaction when the cells were cultured together.

EXAMPLE 3

Unresponsiveness in Secondary Mixed Lymphocyte Reaction

These experiments were performed to determine whether suppression of pre-activated T cells by MSCs resulted in specific unresponsiveness during secondary stimulation.

A. T cells from donor 248 (d 248) were primed by allogeneic PBMCs from donor 273 (d 273) for 7 days, then cultured for 3 additional days alone or in the presence of IFN-γ -treated MSCs from the same donor (d273). Cells were then re-stimulated by the same donor (d273), autologous (d248) or "third party" (d244) PBMCs.

Lymphocyte preparation

Peripheral blood mononuclear cells (PBMC) were prepared by density gradient centrifugation on FICOLL-PAQUE (Pharmacia). Aliquots of cells were frozen in 90% FCS with 10% DMSO and stored in liquid nitrogen. After thawing, the cells were washed twice with MSC medium (DMEM with low glucose and 10% FCS) and re-suspended in assay medium (ISCOVE'S with 25 mM Hepes, 1 mM sodium pyruvate, 100 μM non-essential amino acids, 100

U/ml penicillin, 100 μg/ml streptomycin, 0.25 μg/ml amphotericin B, 5.5×10$^{-5}$M 2-mercaptoethanol (all reagents from GibcoBLR) and 5% human AB serum (Sigma, MLR tested)).

To prepare the T cell-enriched fraction, PBMCs were depleted of monocytes and B cells by immunomagnetic negative selection. PBMCs were incubated with mouse anti-human CD 19 and CD 14 mAbs (no azide/low endotoxin (NA/LE) format) followed by biotin-conjugated goat anti-mouse IgG (multiple adsorption) Ab (all reagents from Pharmingen) and streptavidin microbeads (Miltenyi Biotec). Cells were then separated using a magnetic cell sorter (MACS, Miltenyi Biotec). The T cell-enriched fraction contained about 70–90% CD3+ cells.

MSC culture.

Human MSCs were isolated from bone marrow as described in U.S. Pat. No. 5,486,359 and were maintained in culture with MSC medium and were used at passages from 3 to 6. Cells were lifted using 0.05% Trypsin/EDTA solution, washed once with MSC medium and plated at 70–80% confluent density which was 1×10$^6$/plate for 10 cm tissue culture dish. The day after plating, IFN-γ (Boehringer Mannheim) at 500 U/ml was added and the cells were incubated an additional 3 days. Before transferring T cells, MSC plates were washed 4 times with HBSS, 1 time with ISCOVES, and assay medium was added at 10 ml/well in 10 cm tissue culture dishes.

Primary (1°) MLR.

T cells (d 248) were activated by irradiated PBMCs (d 273). PBMCs used for stimulation were X-ray irradiated with 3,000 rad using Cabinet X ray system (Faxitron X ray, Buffalo Grove, Ill.). For primary stimulation, 2×10$^7$ responders were mixed with 2×10$^7$ stimulators in 20 mls assay medium in 10 cm tissue culture dishes. The cells were incubated at 37° C. in 5% CO$_2$ atmosphere for 7 days.

Activated T cellMSC cultures

T cells activated in the 1° MLR were collected, washed once with MSC medium and re-suspended in assay medium at 10$^6$/ml in 10 ml and were added to 10 cm tissue culture dishes containing autologous or allogeneic MSCs or medium alone, and incubated for an additional 3 days.

Restimulation assay

T cells cultured with MSCs or media were collected, washed once with MSC media, and restimulated with irradiated PBMCs from the original donor, an unrelated donor or autologous PBMCs. For the assay, 5×10$^4$ primed responders and 5×10$^4$ irradiated stimulators were incubated in 96-well plates. Assays were performed in triplicate. Cultures were pulsed with 1

μCi of [$^3$H] thymidine (Amersham) for 18 hours before harvesting. Cultures were collected using Harvester 96 (Tomtec), filters were analyzed using MICROBETA-TRILUX liquid scintillation and luminescence counter (E.G.&G Wallac). Data are presented as mean cpm ± SD of three replicates.

Figure 3:
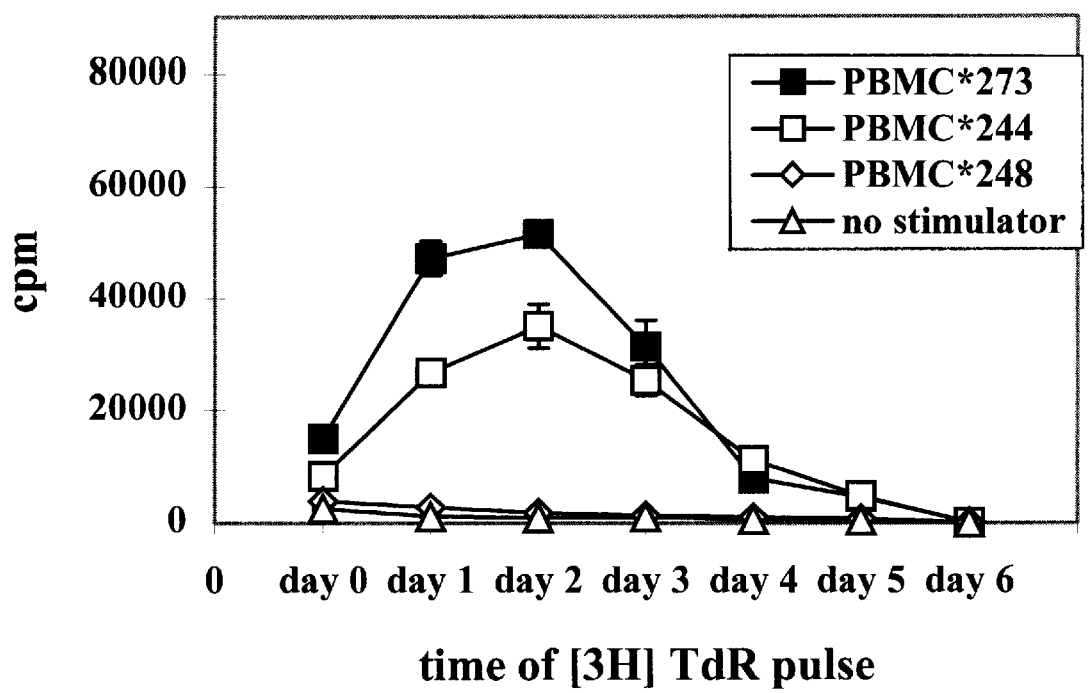
FIG. 3 shows the secondary response of responder T cells primed by stimulator (allogeneic) PBMCs, not exposed to MSCs, and then exposed to autologous PBMCs, allogeneic PBMCs (stimulator or third party) or no cells.
Figure 4:
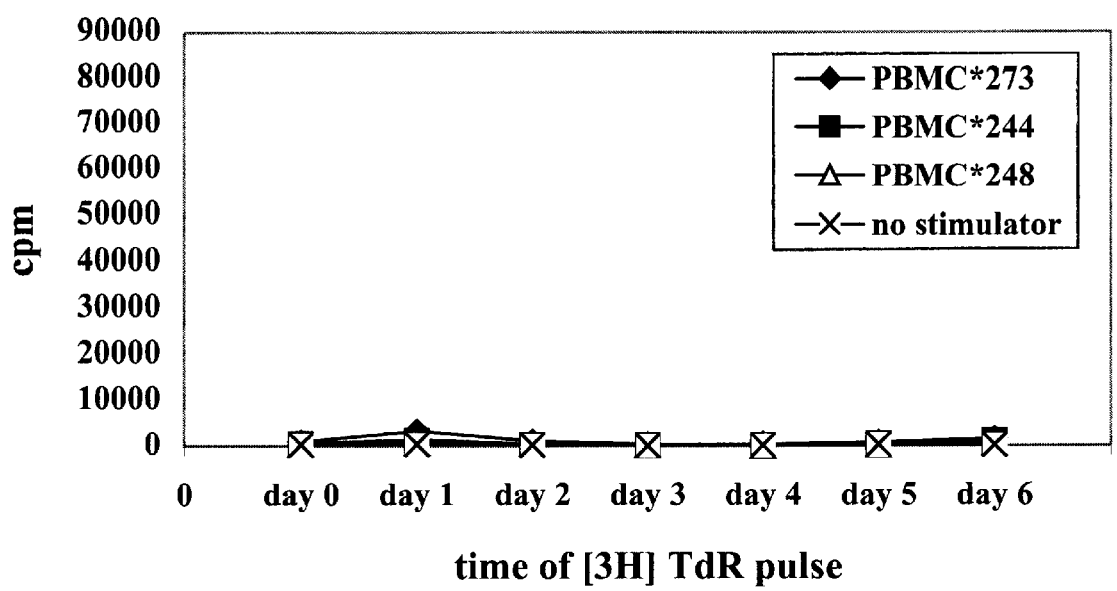
FIG. 4 shows the secondary response of responder T cells activated by stimulator (allogeneic) PBMCs, and subsequently cultured with allogeneic MSCs (stimulator) and then exposed to autologous PBMCs, allogeneic PBMCs (stimulator or third party) or no cells.

T cells cultured alone (positive control) showed an accelerated response to "same donor" re-stimulation with peak at day 2. "Third party" response was also accelerated, practically with the same kinetics as "same donor", but with a lower maximum and a slightly delayed start. (FIG. 3). T cells cultured on allogeneic MSCs subsequently showed no response either to "same donor" or "third party" PBMCs during 6 days of culture (FIG. 4).

EXAMPLE 4

Unresponsiveness in Secondary Mixed Lymphocyte Reaction

T cells from donor 413 were stimulated with irradiated PBMCs from donor 273 for 7 days (1.5×10$^6$ ml each, bulk 20 ml cultures). MSCs from different donors 413, 418 and 273 were plated in 10 cm tissue culture dishes at 1×10$^6$/dish, pretreated with IFN-γ for 3 days and washed prior to mixing with preactivated T cells.

T cells preactivated in the MLR for 7 days were incubated alone or with MSCs for an additional 3 days (1.0×10$^6$/ml T cells, 10 ml/dish). After 3 days of incubation with MSCs, T cells were collected and re-stimulated with irradiated PBMC 273 (original donor), 413 (autologous), PBMC 10 (third party) or PHA (5 μg/ml) in the presence or absence of autologous (d413) PBMC. Cells were added at 5×10$^4$/well, cultures were pulsed with [$^3$H]thymidine at indicated time points for an additional 18 hours.

Figure 5A:
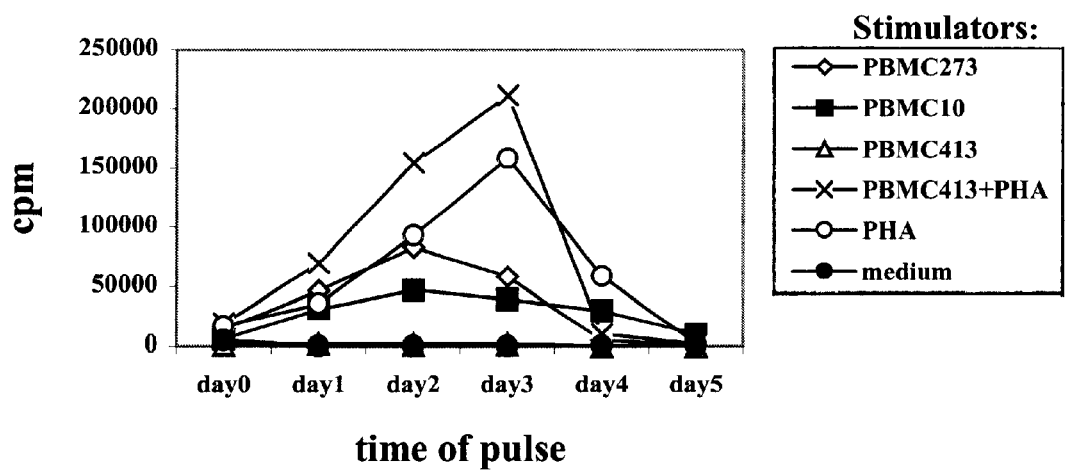
FIG. 5 (FIGS. 5A–5D) shows that the secondary response of responder T cells previously activated by stimulator allogeneic PBMCs and after activation cultured with allogeneic (same donor (FIG. 5B) or third party (FIG. 5D) or autologous MSCs (FIG. 5C) and then exposed to autologous or allogeneic (same donor or third party) stimulator cells was suppressed.
Figure 5B:
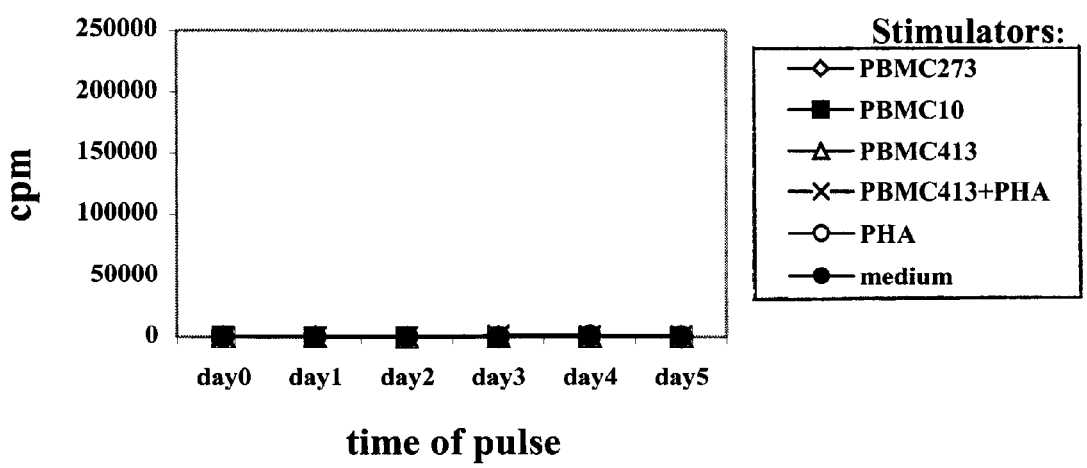
Figure 5C:
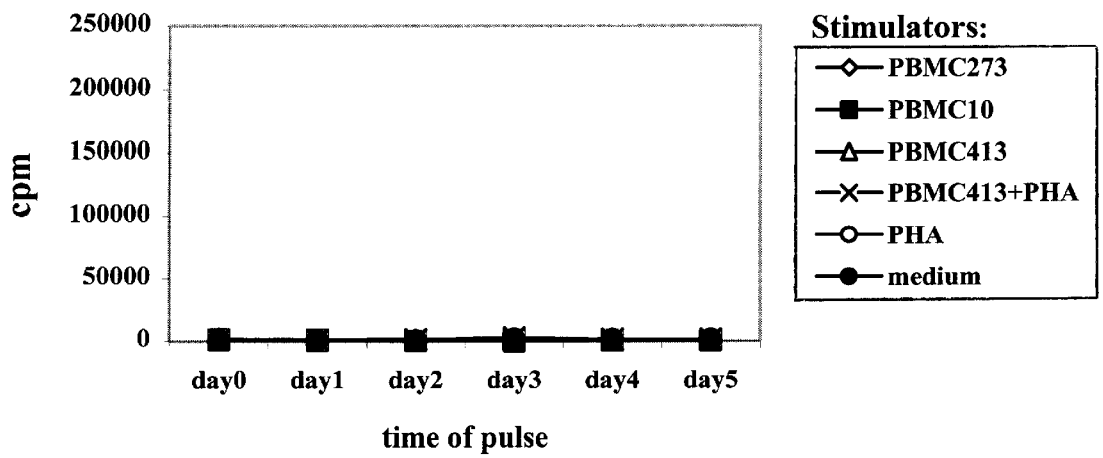
Figure 5D:
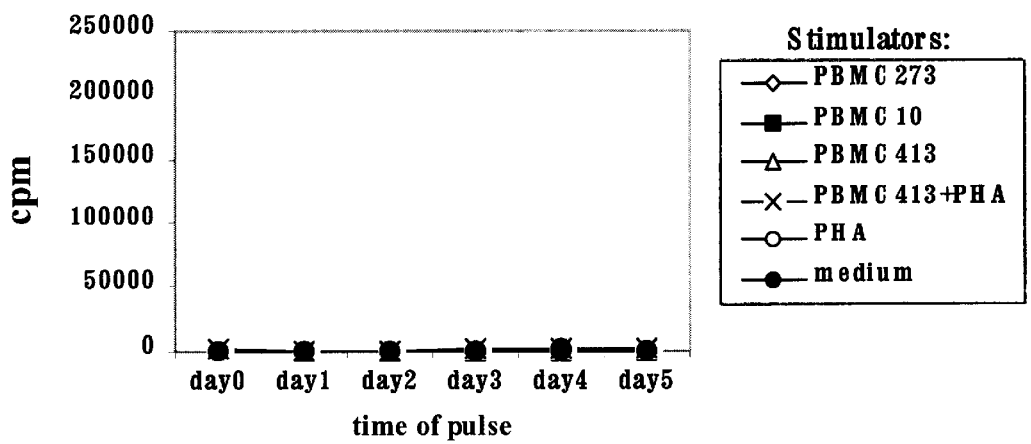
Figure 6A:
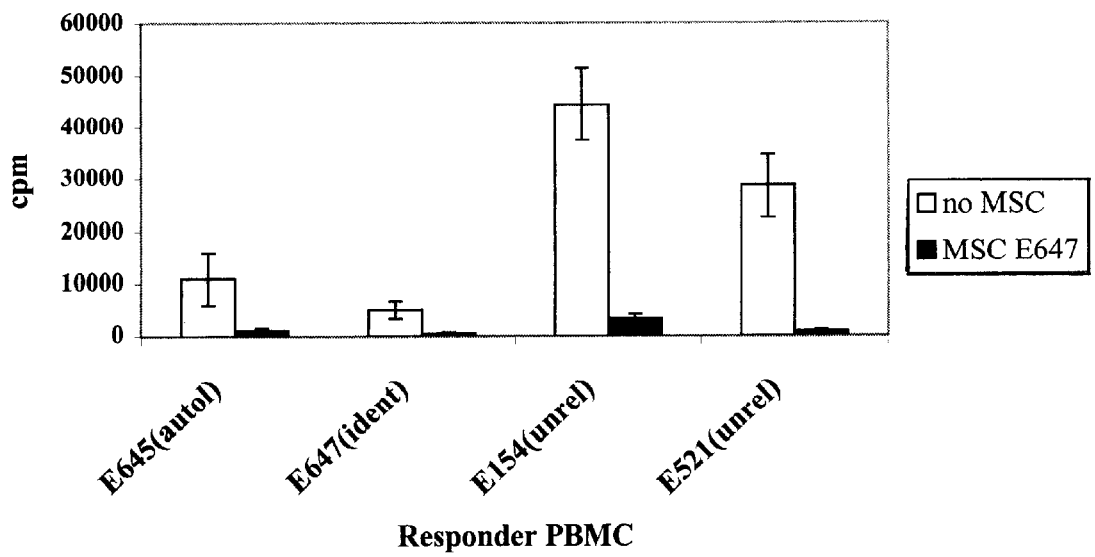
FIG. 6 (FIGS. 6A–6D) shows the suppression of a primary MLR in the canine model by MSCs. autol=autologous; ident=DLA identical litter mates; unrel=unrelated.
Figure 6B:
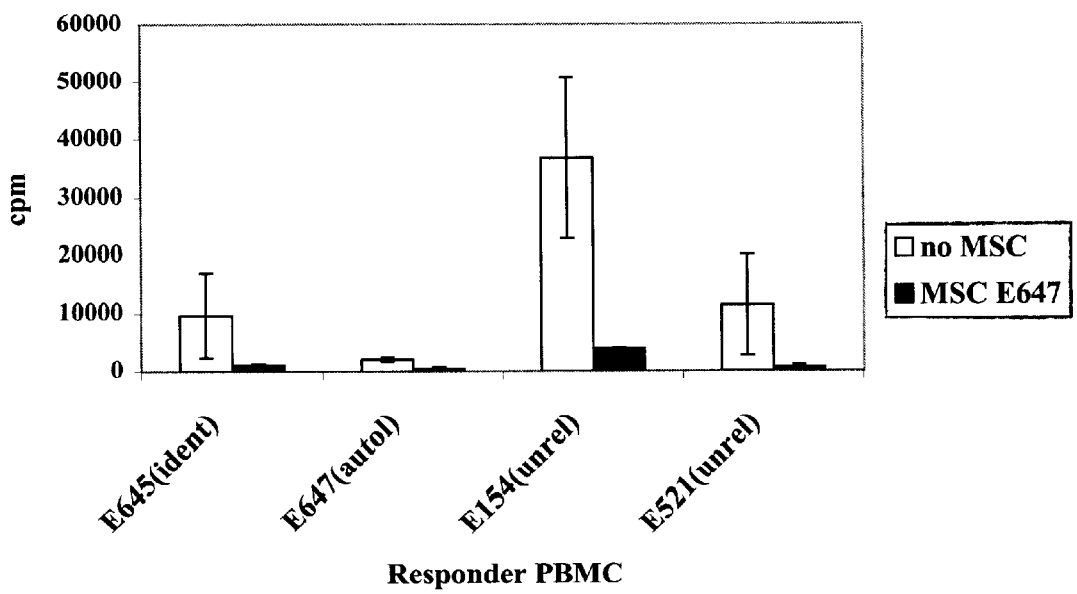
Figure 6C:
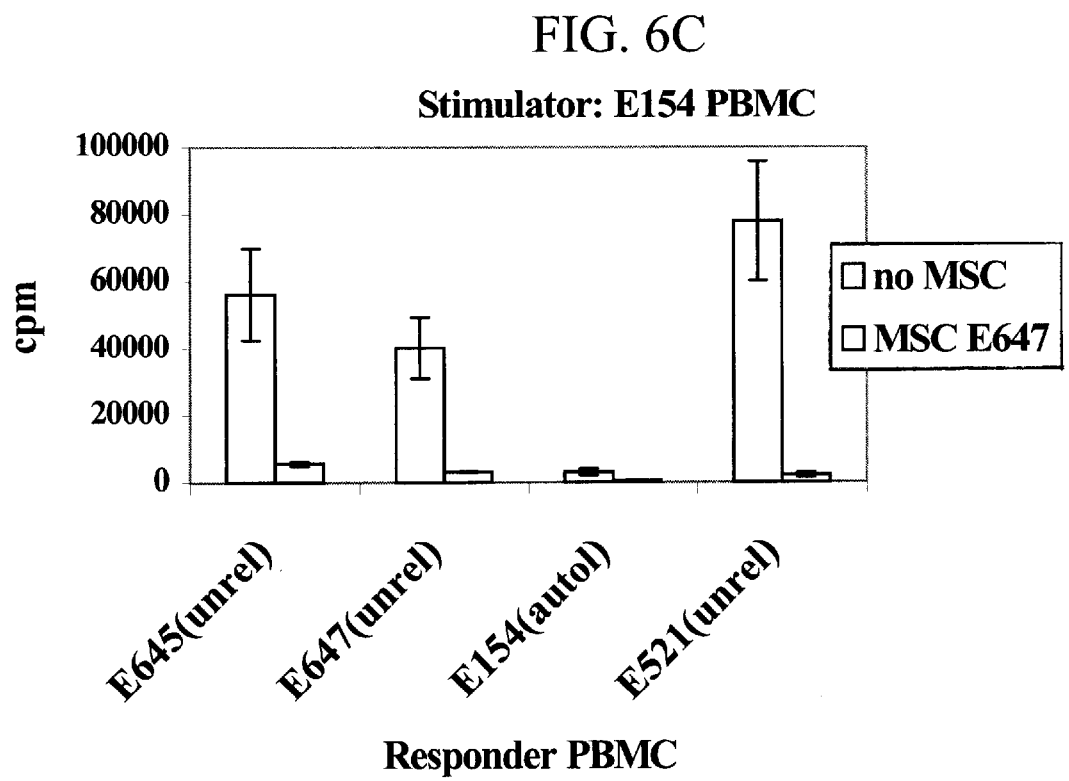
Figure 6D:
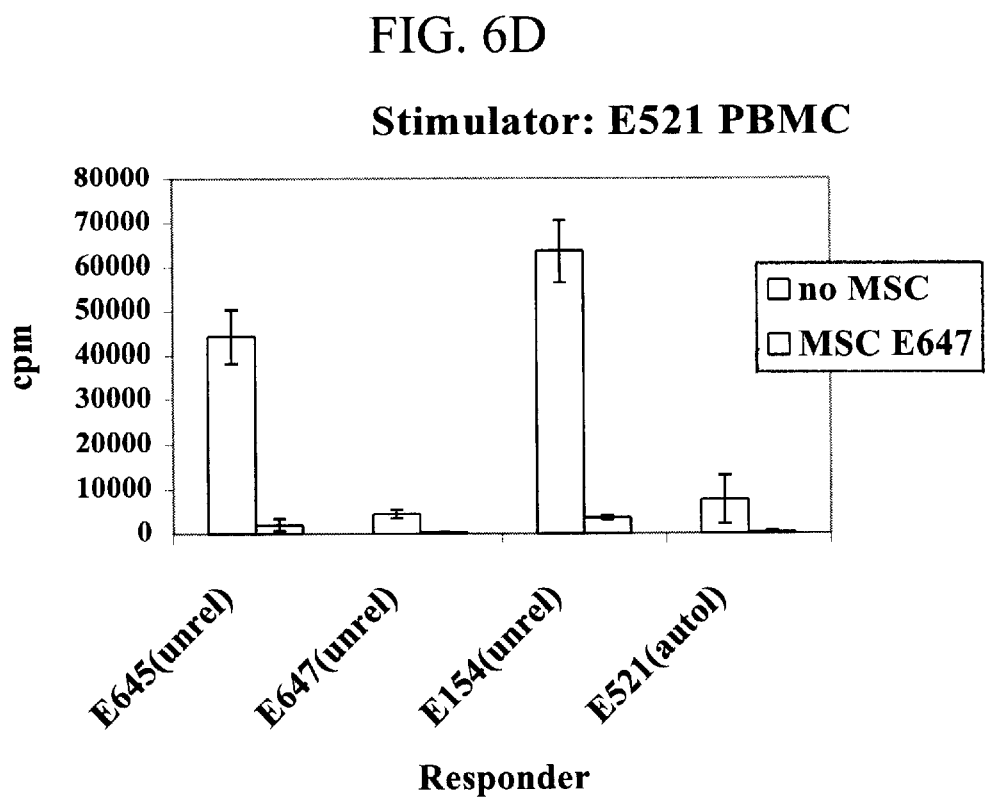

The results indicate that treatment of activated T cells with autologous (d413) (FIG. 5C), same donor (d273) (FIG. 5B) and third party (d418) (FIG. 5D) MSCs induced unresponsiveness to antigenic stimulation in the T cells. The control culture (FIG. 5A) with no MSC treatment showed restimulation of the cells upon exposure to allogeneic PBMCs.

EXAMPLE 5

Suppression of Primary MLR by Canine MSCs

Canine PBMCs were purified from peripheral blood by centrifugation on FICOLL-PAQUE gradient (1.077). Stimulator PBMCs were X-ray irradiated 2200 rad (7 min 70 kV). 10$^5$ irradiated stimulators were mixed with 10$^5$ responder PBMCs in 96-well plates in the presence or absence of pre-plated canine MSC (E647, 2×10$^4$/well). Cultures were incubated for 6 days and pulsed with [$^3$H]TdR (5 Ci/mmol, 1 μCi/well) for an additional 16 hours. Results are shown in FIGS. 6A–6D. E647 and E645 were litter mates (DLA identical). The results showed that autologous as well as allogeneic MSCs suppressed the primary MLR.

EXAMPLE 6

Suppression of Primary MLR by Non-Adherent MSCs

Figure 7:
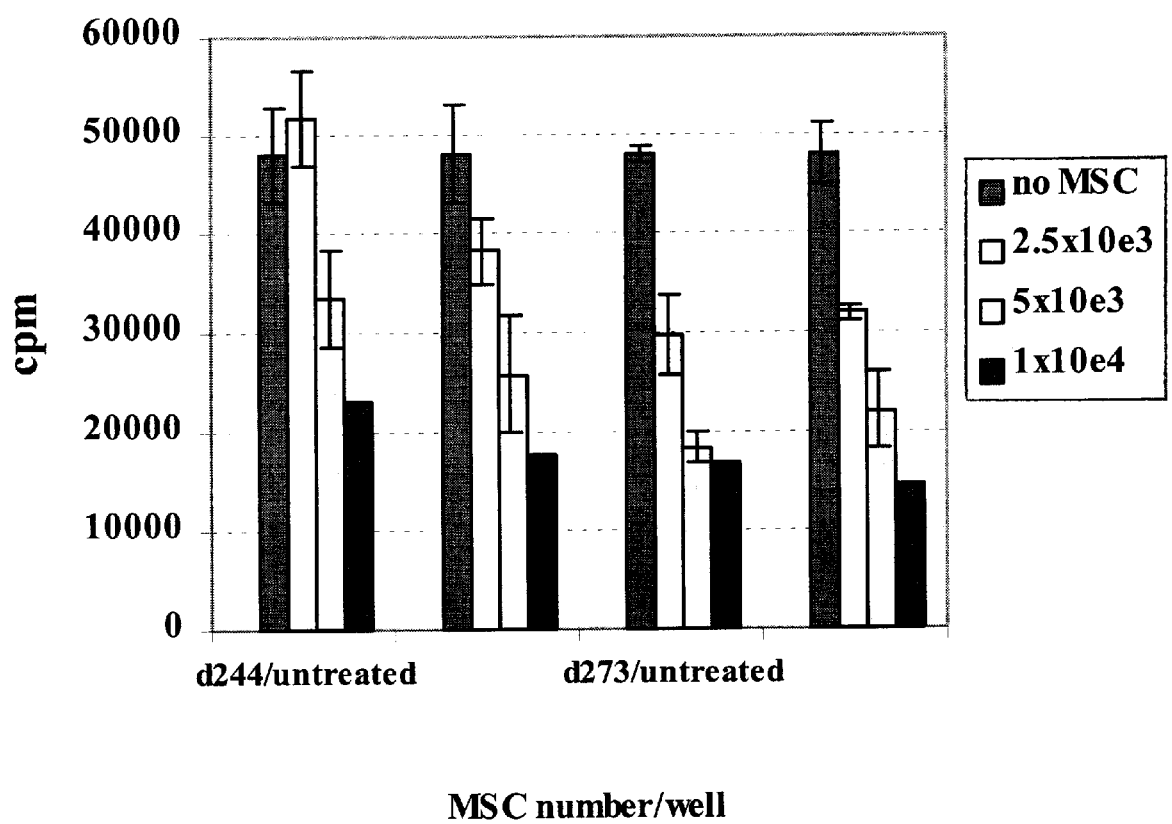
FIG. 7 shows the suppression of a primary MLR by non-adherent MSCs.

T cells from d273 (2×10$^5$/well) were mixed with irradiated PBMCs from d244 (2×10$^5$/well) and different numbers of MSCs. MSCs from dD244 or d273 were pre-treated with IFN-γ (900 U/ml for 3 days) or left untreated, trypsinized on the day of experiment and added at the same time as T cells and PBMCs. Cultures were incubated for 7 days, [$^3$H]TdR (5 Ci/mmol, 1 μCi/well) was added for an additional 16–18 hours. Results are shown in FIG. 7 and demonstrate that non-adherent MSCs also suppressed a primary MLR.

EXAMPLE 7

Allogeneic MSCs Support Skin Allograft Survival

Study Population

Juvenile baboons (*Papio anubis*) were studied. Male and non-pregnant female baboons weighed 7–20 kg and were between 3–16 years of age. They were screened for tuberculosis papilloma virus, titered for cytomegalovirus (CMV), and tested with the primate viral screen consisting of testing for simian virus, and including fecal floatation and smears. Donor and recipient pairs were determined by major histocompatability complex (MHC)-disparity through PCR typing. During the study period, the baboons were housed in an individual area beside a companion animal.

Donor Bone Marrow Harvest for MSC Isolation and Culture-Expansion Needle marrow aspirates were obtained from the iliac crest for isolation and culture-expansion of the MSCs. The marrow aspirate was obtained from an alternate side once a week for four consecutive weeks. The volume of the aspirate was determined by an estimate of 10% of the animal's blood volume. Blood volume (liters) is estimated to be 7% of body weight. A 10 kg baboon then, would have an estimated blood volume of 0.7 liters. An aspirate of 10% of the blood volume would then be 70 milliliters.

Prior to the procedure, 500 mg cefazolin was administered intramuscularly (IM) for perioperative antibacterial prophylaxis. Baboons were sedated and anesthetized for the procedure with ketamine at 10 mg/kg IM, and xylazine 1 mg/kg IM. The sites of needle insertion were scrubbed with povidone-iodine and then rinsed with alcohol. Aspirates were obtained from the iliac crest using a 16-gauge, 2-inch bone marrow needle. A syringe was attached to the needle, and suction was applied to remove the marrow. For postoperative pain, the analgesic Buprenorphine was given at 0.03 mg/kg IM Q12×2 doses.

Shipment of Donor Bone Marrow Aspirates

Bone marrow aspirates were transferred from the syringe to a sterile VACUTAINER® containing sodium heparin. The tubes were placed in a Styrofoam container and shipped at room temperature (RT) by overnight delivery to the cell processing facility.

Isolation and Culture Establishment of MSCs

Five to 10 ml aliquots of bone marrow were diluted to 50 ml in Dulbecco's Phosphate Buffered Saline (DPBS) in a polypropylene culture tube. The cell suspensions were centrifuged at 2200 RPM for 10 minutes at room temperature (RT). Total nucleated cell counts were determined in 4% acetic acid. Cells were then diluted in DPBS for a final concentration of $20 \times 10^6$ cells/ml. Ten ml or $200 \times 10^6$ cells were loaded onto 20 ml of PERCOLL (sp.gr. 1.073 gm/ml) in a 50 ml conical tube and underwent centrifugation at 1300 RPM for 20 minutes. The cell interface containing mononuclear cells was washed in DPBS, resuspended in complete media, and counted to obtain a recovery. The washed mononuclear cells obtained at the PERCOLL interface were cells were then established in T-185 flasks containing 30 ml of complete media and $15-20 \times 10^6$ cells/flask ($8.1 \times 10^4$ MSC/cm$^2$) and placed in a 37° C. incubator at 5% $CO_2$.

Harvest of MSC

The media in the triple flasks was decanted, and the flasks were rinsed with 50 ml DPBS. After decanting the DPBS, 23 ml of 0.05% trypsin was added to each triple flask. The flasks were placed in a 37° C. incubator for 3 minutes. After cell detachment, 23 ml complete medium was added to each flask. The cell suspensions were transferred to 50 ml conical tubes and the flasks were washed with 30 ml HBSS. The tubes were centrifuged at 2200 RPM for 5 minutes at RT.

Formulation/Packaging

The harvested MSCs were formulated at approximately $10 \times 10^6$ cells per ml in cryoprotectant solution consisting of 85% Plasma-Lyte A (Baxter IV Therapy), 10% DMSO, and 5% MSC-donor serum, and cryopreserved in bags containing 15–20 ml.

Labeling/Storage/Shipment

Cells were cryopreserved using a controlled-rate freezer (Cryomed, Forma Scientific) at 1–2° per minute to −90° C. The samples were then transferred to a liquid nitrogen storage freezer in the vapor phase (−120 to −150° C.).

Dose

To achieve an MSC dose of $20 \times 10^6$ cells/kg, the final product was prepared at 115% of the dose required on infusion day.

Skin harvest

Prior to surgery the baboon was given cefazolin at 500 mg IM as a perioperative antibacterial prophylaxis. The baboon was sedated with ketamine at 10 mg/kg IM and anesthetized by intravenous Thiopental induction, a 1–2% isofluorane inhalational anesthetic. Skin was harvested from the anterior abdominal wall, placed on a pre-labeled moistened saline gauze pad. The wound defect was then closed. The baboon was returned to the colony after awakening. For postoperative pain, the analgesic Buprenorphine was administered at Q12×2 doses and Ancef daily for 2 days.

Recipient Skin Transplant and MSC Infusion

Prior to surgery the baboon was given cefazolin at 500 mg IM as an antibacterial prophylaxis perioperatively. The baboon was sedated and anesthetized with ketamine at 10 mg/kg IM and intravenous Thiopental induction, a 1–2% isofluorane inhalational anesthetic. Skin was harvested from the anterior abdominal wall and placed on a pre-labeled moistened saline gauze pad. This skin was divided into two grafts; one was used as the third party control for another recipient baboon and one was used as an autologous control for this same animal. The animal was then placed in a prone position. Three, 3×2-cm sections of skin were removed from the dorsum, along the spine, between the scapulae. The previously harvested skin grafts from the MSC donor, a third party donor and self were defatted, trimmed to fit the skin defects created, and sutured in place.

After grafting, the baboon received an intravenous infusion of MSC at a dose of $20 \times 10^6$ donor MSC/kg. Peripheral blood samples were obtained at pre-MSC, 1 hour, and days 1–3 post-MSC; marrow aspirates were obtained on day 0 post-MSC, day 3, 14, and 30.

For postoperative pain, the analgesic Buprenorphine was administered at Q12×2 doses and Ancef daily for 2 days. The animal was observed daily, and the grafts were photographed every other day beginning on post-graft day 7.

Physical Examinations and Diagnostic Testing

Each baboon was sedated with ketamine 10 mg/kg IM for examination. While sedated, two-three milliliters of marrow were obtained from the iliac crest by needle aspiration and collected in sodium heparin on days 4, 13, and 30, the end of study. A skin biopsy was harvested on the same day that marrow aspirates were obtained.

RESULTS

Effects of MSC Infusion on Skin Allograft Survival

Untreated control animals (N=2) had a mean skin allograft survival time of 8.0±0 days. The infusion of unrelated-MSC-donor MSCs donor (N=2) resulted in a prolongation of skin graft survival time to a mean survival time of 11.5±0.71 days (Mann-Whitney U Test, P<0.05). The infusion of unrelated-third-party donor MSC on donor allografts (N=4) resulted in a significant prolongation of skin graft survival times to a mean survival time of 12.3±0.96 days (Mann-Whitney U Test, P<0.003).

Recipients 6140 and 6200 received allografts from the MSC donor 6243, from each other (a third party graft), and from themselves (an autograft). Twenty-four hours prior to skin graft harvesting from the MSC donor, 6243, MSCs from 6243 were injected under the anterior abdominal skin which had been delineated for grafting. After grafting, the recipients were administered an intravenous infusion of $20 \times 10^6$ MSC/kg (6243). Both third-party allografts were rejected on day 13. The MSC-donor (6243) allografts were found to be hemorrhagic on day 4, a finding usually attributed to a technical failure. On pathologic examination, keratin was noted to have been insinuated in a track-like fashion, below the dermis: the nature of these tracks suggests these were formed by the needle at the time of subcutaneous MSC injection. The presence of these cells had elicited a tremendous inflammatory response. This inflammatory response precluded the ability of the skin grafts to adhere/"take" properly and these grafts were completely necrosed by day 7. The autografts were not rejected.

Recipients 6654 and 6659 received allografts from the MSC donor 6593, from each other (a third-party graft), and from themselves (an autograft). After grafting, the recipients were administered intravenous infusions of $20 \times 10^6$ MSC/kg. The MSC-donor allografts were rejected on days 11 and 12, and the third-party donor allografts were rejected on days 11 and 12. The autografts were not rejected.

Similarly, recipients 6663 and 6658 received allografts from the MSC donor 6656, from each other (a third-party graft), and from themselves (an autograft). After grafting, the recipients were administered intravenous infusions of $20 \times 10^6$ MSC/kg. The MSC-donor allografts were rejected on day 11, and the third-party donor allografts were rejected on days 10 and 12. The autografts were not rejected.

Recipients 6532 and 6720 in the control arm of the study received auto- and allografts without the administration of MSC by infusion or injection. Their allografts were rejected on day 8. The autografts were not rejected.

There were no identifiable toxicities associated with allogeneic MSC infusion and no adverse clinical sequelae in the subsequent 30-day follow-up interval. Blood samples were obtained at pre-MSC, 1 and 2 hours, and days 1, 2, and 3 after grafting and MSC infusion. Marrow aspirates were obtained on days 4 and 13 after grafting and MSC infusion.

These results demonstrate that a single infusion of allogeneic baboon MSCs can delay rejection of allogeneic skin grafts. No other immunosuppressive therapy was administered. One dose of allogeneic or third party MSCs increased the time to rejection by 50% (standard rejection time in this model is 8 days (See Goodman et al. *Am Surg* 62(6):435–42 (1996)).

EXAMPLE 8

The purpose of the study was to demonstrate the feasibility and safety in dogs of the infusion of a moderately high dose of donor dog leukocyte antigen (DLA)-identical littermate canine mesenchymal stem cell (cMSC) at $10 \times 10^6$ cells/kg in an allogeneic marrow graft setting. A secondary objective was to examine the distribution and function of donor neo- and GFP-marked cMSC at 50 and 100 days post-transplant.

MATERIALS AND METHODS

Experimental animals

Beagles were used for the study. Two male and two female DLA-identical littermates were used in the study, aged 7 or 9 months on day 0. The method for typing used involves the use of highly polymorphic microsatellite markers to follow inheritance of the Class II DRB region in the Dog Leukocyte Antigen (DLA), the canine equivalent of the major histocompatability complex. Microsatellites are small di- tri- or tetra nucleotide repeats, which show sufficient length variation in alleles that they may be used to follow inheritance of chromosomal segments through multigeneration crosses. Segregation of alleles is typically monitored using a single-step polymerase chain reaction with primers derived from unique sequences of DNA that surround each repeat. In addition, mixed leukocyte reactions were performed on the DLA-identical littermate pairs chosen for study to provide confirmation of the PCR microsatellite marker assay results.

Study Design

The dogs underwent transplantation with cMSC and bone marrow from the same DLA-identical littermate donor. The marrow graft was harvested from each of the two DLA-identical littermates on day 0 prior to total body irradiation (TBI) and exchanged. Myeloablation was induced by exposing the dogs on day 0 to a single TBI dose of 920 centigray (cGy) (midline air exposure from two opposing $^{60}$Co sources delivered at a rate of 7 cGy (9.3R)/min. Culture-expanded cMSC isolated from a donor marrow aspirate at 4 or more weeks prior to transplantation, were transduced with Papp@OT-24, containing the genes for green fluorescence protein (GFP) and neomycin phosphotransferase (neo). The cMSC were cryopreserved after passage 1 (P1) or passage 2 (P2). Following TBI, the cMSC were thawed and delivered intravenously via a portable infusion pump over a 15-minute time period. Within one to two hours after cMSC infusion the bone marrow graft was infused intravenously at a dose of $\geq 1 \times 10^8$ total nucleated cell (TNC)/kg.

Cyclosporin was administered to all four dogs for graft-versus-host-disease (GVHD) prophylaxis intravenously on days 0 through 5 at a dose of 10 mg/kg BID (20 mg/kg/day) (SANDIMMUNE® Injection Solution, Sandoz Pharmaceuticals Corporation). On days 6 through 50 (end of study) for group I.1.a, or 6 through 100 for group I.1.b, cyclosporin was administered at 10 mg/kg BID PO, (20 mg/kg/day) (NEORAL® Soft Gelatin Capsules, Sandoz Pharmaceuticals Corporation). The usual supportive care with oral antibiotics for the recipient began on day −5 and systemic antibiotics started on day 0 and continued until engraftment was achieved. Fluid support was given as necessary. No platelet transfusions were required for any of the four dogs during recovery. Standard canine procedures require that a whole blood transfusion to be administered if the platelet count consistently drops below 10,000/mm$^3$, or if the treatment staff observes signs of bleeding. Platelet transfusions, if necessary, were to be administered as 50-ml of whole irradiated (2000 cGy) blood from a random donor. Engraftment was established as the time of the first of three consecutive measurements of >500 absolute neutrophil cells mm$^3$, >1,000 /mm$^3$, and platelets >10,000 /mm$^3$, 50,000/ mm$^3$, and >100,000.

To follow hematopoietic recovery, complete blood counts (CBCs) were obtained from day 0 through day 50, and biweekly thereafter for the 100-day study group. Serum chemistry analysis was performed on days 0, 2, and weekly thereafter. Peripheral blood samples were taken on day 0 pre-MSC infusion, 5- and 15-minutes, 1- and 2-hours, and I-, 2-, 3-, and 4-day time points for DNA isolation. The DNA was evaluated for the presence of GFP marked cells by an Anti-EGFP DNA PCR Elisa with digoxigenin incorporated into the product and a second step anti-digoxigenin colorimetric assay. A marrow aspirate was obtained when the platelet counts consistently reached 50,000/mm$^3$ and examined for the presence of GFP marked cells using the same PCR method. CMSC cultures were established to examine colony forming units (CFU), and to expand the cMSC for further Anti-EGFP PCR analysis. Upon necropsy, peripheral blood, bone marrow aspirates, and bone marrow biopsies were obtained for Anti-EGFP PCR analysis. CFU assays were performed on the bone marrow aspirates, and the Anti-EGFP PCR analysis was performed on culture-expanded cMSC. An histological analysis was performed for the presence of GFP in various tissues.

cMSC isolation, culture-expansion, transduction and cryopreservation

Bilateral bone marrow aspirates were obtained for cMSC isolation and culture establishment on week-4 for dogs CAN-07-01 and CAN-07-02 and on week-9 for dogs CAN-07-03 and CAN-07-04. Fifteen ml of marrow (7 ml from each humerus) were obtained from each dog. Dogs were anesthetized by the injection of Butorphanol followed by injection of a mixture of Diazepam and ketamine hydrochloride (Aveco Co., Inc., Fort Dodge, Iowa). The sites of needle insertion were scrubbed with povidone-iodine and then rinsed with alcohol. Aspirates were obtained from each humeral condyle of each dog using a 16-gauge, 2-inch bone marrow needle. A syringe was attached to the needle, and suction was applied to remove 8 ml of marrow from each humerus. Bone marrow aspirates were transferred to 15 ml polypropylene conical tubes using sterile technique. Following the procedure, the dog was then placed on a warming pad to recover.

Five to 10 ml aliquots of bone marrow were diluted to 50 ml in Dulbecco's Phosphate Buffered Saline (DPBS) in a polypropylene culture tube. The cell suspensions underwent centrifugation at 2200 RPM for 10 minutes at room temperature (RT). Total nucleated cell counts were determined in 4% acetic acid. Cells were then diluted in DPBS for a final concentration of $20 \times 10^6$ cells/ml. Ten ml or $200 \times 10^6$ cells were loaded onto 20 ml of PERCOLL (sp.gr. 1.073 gm/ml) in a 50 ml conical tube and underwent centrifugation at 1300 RPM for 20 minutes. The cell interface containing mononuclear cells was washed in DPBS, resuspended in complete media, and counted to obtain a recovery percentage. The cells were then diluted in complete media, cultures were established as described below, and placed in a 37° C. incubator at 5% $CO_2$.

Construction of bicistronic MuL V retroviral vector

Figure 8:
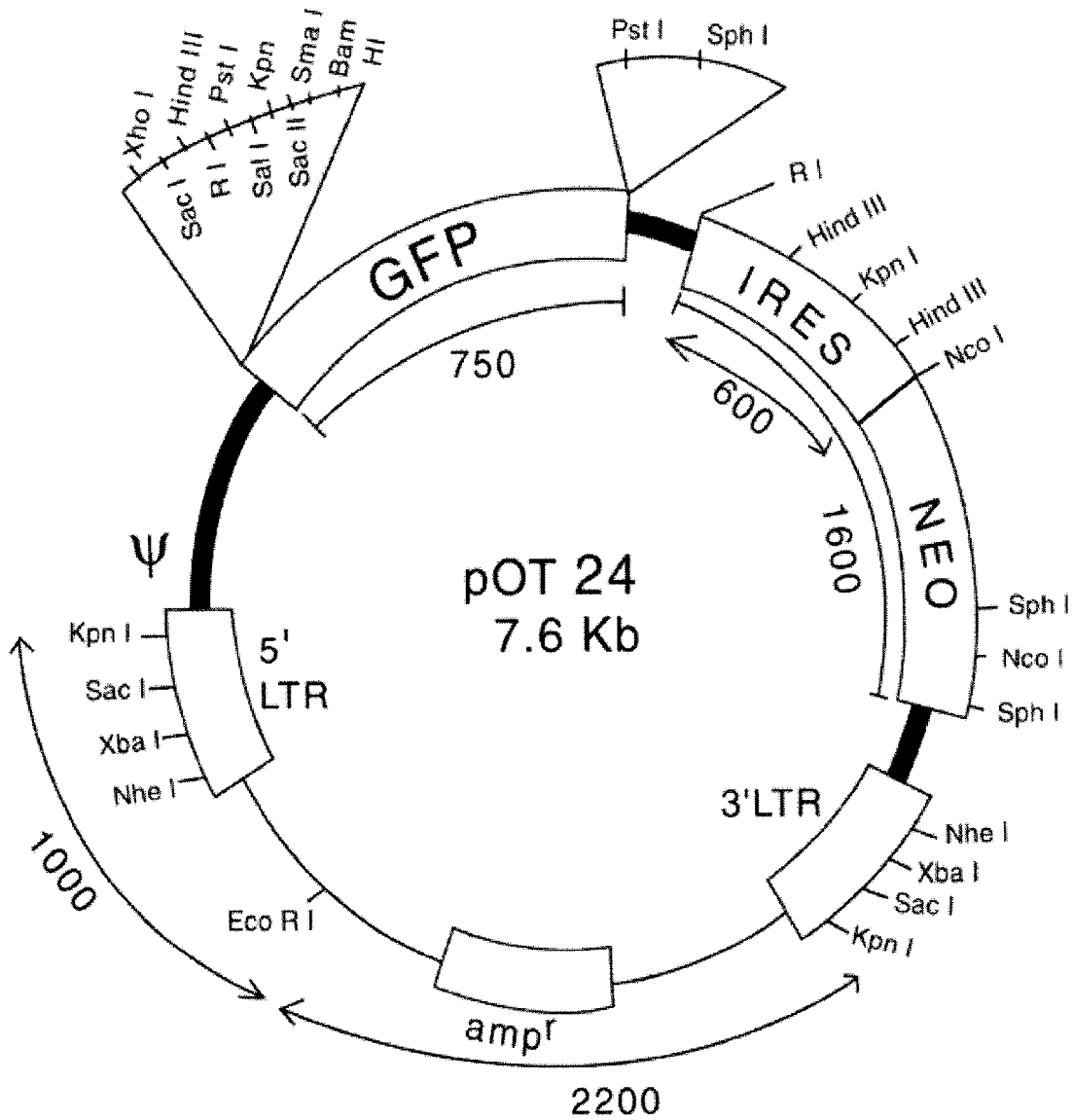
FIG. 8 shows a schematic map of EGFP pOT24 plasmid used in Example 8.

The green fluorescent protein (EGFP) retrovirus was constructed by isolating EGFP-1 gene from the jellyfish *Aequorea victoria* (Clontech, Calif.). EGFP gene was cloned into retroviral vector pJM573-neo (resulting plasmid was named pOT-24). The plasmid pJM573-neo was derived from pN2 (Keller et. Al., 1985, *Nature* 318:149) with the following modifications: murine retroviral gag initiation site was substituted with an in-frame stop codon; 5'LTR and 3'LTR were constructed into the same cassette; neomycin phosphotransferase gene (neo) and an internal ribosomal entry site (IRES) were inserted into pN2. A schematic map of EGFP pOT24 plasmid is shown in FIG. 8.

Preparation of Recombinant Retrovirus pOT-24 was transfected into GP&E86 ecotropic producer cells using DOTAP® (Boehringer Manheim) as suggested by manufacturer. The transfected cells were grown in DMEM-high glucose (HG) medium supplemented with 10% heat inactivated FBS, PenicillinStreptomycin (Life Technologies) and 0.5 mg/ml of protamine sulfate-G418 (Sigma) as a selective marker. Cultures were maintained up to 70% confluency at which point medium was replaced with fresh retroviral media (without G418) and cells were maintained at 32° C. for 2 days. The culture medium containing the retrovirus was collected, filtered through 0.45 μm filter and stored at -70° C. Amphotropic retrovirus was prepared by transducing PA317 cells twice with ecotropic virus using a centrifugal transduction procedure followed by selection with G418 (0.5 mg/ml). Retroviral supernatant was collected. The titer of the pooled EGFP retrovirus on 3 T3 cells was $1.2 \times 10^6$ CFU/ml. GFP-retroviral supernatants were cryopreserved at -70° C.

CAN-07-01 and CAN-07-02

The washed mononuclear cells obtained at the PERCOLL® interface were established in 10, T-185 flasks containing 30 ml of complete media and $10 \times 10^6$ cells/flask.

On days 2, 6, and 9 of culture, the media in the flasks was replaced entirely with fresh complete media. On day 12 of the primary culture photographs were taken, and the cells were taken from passage 0 (PO) to passage 1 (P1). The media was aspirated and the flasks were washed twice with 8 ml DPBS. Eight ml of trypsin was added, and flasks were placed in a 37° C. incubator for 3 minutes. When the cells had lifted, the reaction was stopped by the addition of 8 ml of complete media. The cells were transferred and pooled into 50 ml conical tubes. The flasks were washed with DPBS and the pooled cells were centrifuged at RT at 2000 RPM for 5 minutes. The supernatant was removed and the cell pellets were resuspended in complete media. The cells were pooled, counted and examined for viability. Cells were plated into 15, T80 flasks containing 18 ml of complete medium and $0.4 \times 10^6$ cells per flask.

On day 15 in culture, the first transduction was performed on 15 of the 18 flasks. The media was removed. Aliquots of the retroviral supernatant were thawed and polybrene was added to a final concentration of 8 μg/ml to make the transduction cocktail. The cell medium was replaced with 10 ml of the transduction cocktail, and the flasks were centrifuged at 3000 RPM for 1 hour at 32° C. After centrifugation, 10 ml of complete media prepared using heat inactivated fetal bovine serum (FBS) was added to each flask (with the transduction cocktail) and the flasks were returned to the incubator. Three flasks were not transduced, and fresh media was replaced. On day 16 of culture, the media was replaced with fresh complete media. On day 17 of culture the transduction procedure was repeated.

On day 18 of culture, the cells were harvested as described above and taken from P1 to P2. Three$\times 10^6$ cells were added to 100 ml of complete medium, and poured into triple-flasks (500 cm$^2$). Fifteen triple-flasks were prepared with transduced cells and three were prepared with untransduced cells. Any remaining cells were cryopreserved. A freeze solution was prepared containing 10% DMSO and 90% FBS. Ten$\times 10^6$ cells were resuspended in 1 ml of freezing solution. The vials were labeled and cryopreserved in a Nalgene Cryo container for a minimum of 4 hours at -70° C., and stored at -70° C.

On day 22 of P2 culture, photographs were taken to record the cell distribution and morphology and the P2 cells were harvested and cryopreserved as described below.

CAN-07-03 and CAN-07-04

The washed mononuclear cells obtained at the Percoll interface were established in 15, T75 flasks containing 20 ml of complete media and $12 \times 10^6$ cells/flask.

On day 2 of culture, the media in the flasks and in the dishes was replaced entirely with fresh complete media. On day 6 of primary culture for cMSC, the first transduction was performed as described above. Three flasks were not transduced, and fresh media was replaced on day 6. On day 7 of culture, the media was replaced with fresh media.

On day 8 of culture the transduction procedure was repeated. On day 9 in culture, photographs were taken, and the cells were passaged from P0 to P1 as described above. Three$\times 10^6$ cells were added to 100 ml of complete medium, and poured into triple flasks. Fifteen triple flasks were prepared with transduced cells and three were prepared with untransduced cells.

The 15 ml bone marrow aspirates yielded 910, 1212, 856, and $1948 \times 10^6$ nucleated cells for donors CAN-07-01, CAN-07-02, CAN-07-03, and CAN-07-04, respectively. Mononuclear cell counts obtained from the PERCOLL interface were 612, 666, 588, and $462 \times 10^6$, resulting in recoveries of 67.2, 55, 68.7, and 23.7%. Upon P1, the cell viability was a mean of 97.1 (range 93.3 to 100)%. Upon P2 for donors CAN-07-01 and CAN-07-02, and P1 cells for donors CAN07-03 and CAN-07-04, the cell viability of the transduced cells was a mean of 96.7 (range 96.3 to 97.9)%. The untransduced cells were 95.4 (range 93.3 to 96.9)% viable. Upon harvest for cryopreservation of the cMSC, the viability of the transduced cells was a mean of 99.4 (range 97.4 to 100)% and the untransduced cells were 99.4 (range 97.6 to 100)% viable (Table 4).

The transduced cMSC yield per flask for donors CAN-07-01 and CAN-07-02, harvested 4 days after passage 2 and plated at $3\times10^6$ per flask was 5.9 and $6.7\times10^6$, and the untransduced cMSC yield per flask was 8.4 and $7.5\times10^6$. The transduced cMSC yield per flask for donors CAN-07-03 and CAN-07-04, harvested 4 days after passage 1 (different transduction and passage design) and plated at $3\times10^6$ per flask was 20.0 and $14.0\times10^6$, and the untransduced cMSC yield per flask was 25.3 and $18.0\times10^6$.

CFU Assays on cMSC from P0 Cultures

CFU colony assays were prepared at the time of primary culture establishment by plating $0.5\times10^6$ cells in triplicate in 100 mm dishes containing 10 ml complete media. The dishes were incubated at 37° C. and 5% $CO_2$. The media was replaced with fresh media each 2 to 4 days. On day 10 in culture, the CFU assay dishes were rinsed with HBSS twice, fixed with 1% gluteraldehyde for 15 minutes, rinsed with HBSS twice, and air dried. The cMSC in the dishes were then stained with 0.1 % crystal violet, rinsed with deionized water three times, and air dried. Colonies were counted to calculate the number of colonies forming per $10^6$ cells plated.

CFU assays plated on day of mononuclear cell isolation and culture establishment and harvested on day 10 yielded 56, 46.7, 114, and 72 colonies per $10^6$ cells for dogs CAN-07-01, CAN-07-02, CAN-07-03, and CAN-07-04, respectively.

On day 13 of P1 culture, photographs were taken to record the cell distribution and morphology and the P1 cells were harvested by trypsinization and cryopreserved as described below.

The media in the triple flasks was decanted, and the flasks were rinsed with 50 ml DPBS. After decanting the DPBS, 23 ml of 0.25% trypsin was added to each triple flask. The flasks were placed in a 37° C. incubator for 3 minutes. After cell detachment, 23 ml complete medium was added to each flask. The cell suspensions were transferred to 50 ml conical tubes and the flasks were washed with 30 ml HBSS. The tubes were centrifuged at 2200 RPM for 5 minutes at RT. The pellets containing the transduced or untransduced cells, respectively, were pooled and counted. One aliquot of $1\times10^7$ cells was set aside for determination of the transduction percentage by an Anti-EGFP DNA PCR Elisa assay.

After harvest, the recovered P1 or P2 transduced and culture-expanded cMSCs centrifuged at 1300 RPM for 5 minutes and resuspended in 1 ml aliquots with $1\times10^7$ cMSC/ml in ice-cold cryoprotectant solution containing 85% Plasma-Lyte A (Baxter IV Therapy), 10% DMSO, and 5% autologous canine serum. Cell aliquots were dispensed into separate cryo-vials containing 1 ml each. The tubes were labeled with the canine donor number and total viable cell count. The cMSCs were cryopreserved by placing the cell vials into a Nalgene freezing container and placed in a −70° C. freezer for 4 hours, then moved to storage at −70° C.

Upon cell harvest for cryopreservation of the product, aliquots of $1\times10^7$ cells were obtained for determination of the transduction efficiency. The transduction efficiency was analyzed by an Anti EGFP DNA PCR Elisa with digoxigenin incorporation into the product and a second step Anti-digoxigenin colorimetric assay.

CMSC Infusion Product

One to two hours before infusion, the vials of cMSC were thawed by swirling in a 37° water bath, sprayed with 70% ethanol, and opened in a biosafety cabinet. The cMSC product was suspended in 50 ml of infusion medium containing DMEM-LG plus 30% serum autologous to the cell donor. The viability of the cMSC product was determined by exclusion of trypan blue to determine the actual viable dose. An aliquot of each cMSC product was submitted for yeast isolate, aerobic, and non-aerobic growth. The cMSCs were evaluated for the ability to attach to tissue culture plastic and to proliferate in P2 (P3 for CAN-07-01 and CAN-07-02) culture. Aliquots of $1\times10^6$ and $0.16\times10^6$ cMSC were plated into complete canine culture medium in triplicate in T-25 plastic culture flasks. After 24 hours, the flasks plated with $1\times10^6$ cMSC and on day three, the flasks plated with $0.16\times10^6$ cMSC were harvested by trypsinization and counted.

Following TBI, the cMSC suspension was infused via a catheter inserted into the cephalic vein using a hand-held Harvard Bard Mini Infuser to deliver the 50 ml over a 15–20 minute period.

Moderately high doses of 7.49, 7.35, 10.0, and 10.0 (mean $8.7)\times10^6$ viable cMSC/kg were infused on day 0 to dogs CAN-07-01, CAN-07-02, CAN-07-03, and CAN-07-04, respectively. These doses represent a 4- to 10-fold increase over the typical dose that a patient would receive. Total viable cMSC infused ranged from 67.7 to 129 (mean 93.9)$\times 10^6$ cMSC. The viability of the cells ranged from 92.1 to 97.6 (mean 94.9) as determined by trypan blue exclusion. CMSC Infusions were given between 71 and 146 (mean 110) minutes post-TBI.

Blood Sampling Post-Infusion

Blood samples (2 ml) were obtained before (pre) and during the cMSC infusion at five and fifteen minutes after the start of the infusion, as well as 1- and 2-hour, and 1-, 2-, 3-, and 4 day time points. Cell lysates were prepared using the PURGENE™ (Gentra Systems, Inc.) DNA Isolation Kit for use in an Anti EGFP DNA PCR Elisa with digoxigenin incorporated into the product and a second step Anti-digoxigenin colorimetric assay to detect of the level of GFP marked cMSC in the bloodstream.

Bone marrow harvest and graft infusion

Bone marrow to be used as the transplant graft was harvested from the DLA-identical littermate prior to TBI. Aspirates were obtained from each humerus using an 11-gauge, 4–6 inch ball-top stainless steel marrow harvest needle, attached to polyvinyl tubing originating from a vacuum flask containing 100 ml Tissue Culture Medium 199 and 4 ml (4000 U) heparin. The marrow is passed through 300- and 200-um pore size, and stored at 4° C. in a transfer pack container, labeled with the donor and recipient, until infusion later that day. The bone marrow total nucleated cell count (BM-TNC) of the marrow is corrected to exclude any nucleated cells which would be present in the volume of peripheral blood obtained during the marrow harvest.

The total nucleated cell count (TNC) of the bone marrow was corrected to exclude any TNC which would be present in the volume of peripheral blood obtained during the marrow harvest. Corrected doses of marrow were 4.3, 3.5, 3.1, and 2.0 (mean 3.2)$\times 10^8$ TNC/kg to dogs CAN-07-01, CAN-07-02, CAN-07-03, and CAN-07-04, respectively. Uncorrected bone marrow doses were 5.6, 4.2, 4.5, and 2.7 (mean 4.3)$\times 10^8$ TNC/kg.

Twenty minutes prior to infusion, the marrow was placed at room temperature. One hour after the cMSC infusion, the marrow was infused intravenously through a butterfly needle inserted into the cephalic vein, by exerting pressure on the bag over 1 to 2 minutes.

Supportive care

On day −5, oral antibiotics (neomycin sulfate and polymyxin sulfate) were given three times daily. These oral antibiotics were administered until absolute neutrophil counts reached 500/mm$^3$. On day 0, the systemic antibiotic Baytril was administered intravenously twice daily and continued until absolute neutrophil counts reached 1,000/mm$^3$ consistently. Fluid and electrolytes lost as results of transient radiation toxicity were replaced by subcutaneous administration of 500 ml of Ringers Solution, twice daily until food and water were accepted.

Differential blood cell counts

Blood samples (2 ml) were collected from either the jugular or cephalic vein on the mornings of the marrow aspirate for isolation of cMSC, days 0 through 50 and biweekly thereafter through the end of study. The blood was transferred into a VACUTAINER containing EDTA. Total white blood cell (WBC) and platelet counts per mm$^3$ are measured using a Sysmex E2500 and differential cell counts were determined manually after fixation and staining with Wrights stain.

Necropsy

Blood samples were obtained for CBC, Chemistry 23 analysis, and PCR evaluation. The dogs were sedated with Butorphanol followed by a mixture of Diazepam and ketamine hydrochloride. After sedation, biopsies and bilateral bone marrow aspirates were obtained from the HUMERI, femora, and iliac crests. Euthanasia was then completed with an overdose of the sedative sodium pentobarbital. The day-50 group of dogs (CAN-07-01 and CAN-07-02) were euthanised on day 43 in the study; the day-100 group of dogs (CAN-07-03 and CAN-07-04) were euthanised on day 100 in the study. Complete sets of the tissues were collected upon necropsy of the animals.

The collection of tissues for histological examination followed immediately. A subset of tissues was used for Anti-EGFP DNA PCR Elisa analysis. Bone marrow aspirates and biopsies were used for Anti-EGFP DNA PCR Elisa analysis, culture expansion for further PCR analysis, and CFU assays The tissues were trimmed to about 1 inch square pieces and placed into separate labeled 50 ml conical tubes filled with 10% Neutral Buffered Formalin (pH 6.8–7.2). The tissues were embedded in paraffin, sectioned and stained with Hematoxylin and Eosin. Bone marrow samples were stained with Periodic Acid Schiff's stain.

Bone marrow aspirates obtained prior to necropsy were collected in 15 ml labeled tubes from the left and right humeri, femora, and iliac crests from each dog. A subset of the tissue samples were obtained during necropsy and trimmed to about ¼ inch square pieces, wrapped in PBS-soaked gauze and placed separately in a labeled zip-lock bag. The bone marrow aspirates were held on ice.

Preparation of bone marrow aspirates for CFU assay

Aliquots of the bone marrow aspirates from the left and right humerus, femur, and iliac crest from each canine obtained for PCR analysis were aliquoted into separate 15 ml labeled tubes. The bone marrow samples were held on ice.

CFU assay on cMSC from bone marrow obtained at necropsy

CFU colony assays performed on cMSC obtained from bone marrow obtained at necropsy were prepared by plating 0.5×10$^6$ cells in triplicate in 100-mm dishes containing 10 ml complete media. The dishes were incubated at 37° C. and 5% $CO_2$. The media was replaced with fresh media each 2–4 days. On day 10 in culture, the CFU assay dishes were rinsed with HBSS twice, fixed with 1% gluteraldehyde for 15 minutes, rinsed with HBSS twice, and air dried. The cMSC in the dishes were then stained with 0.1% crystal violet, rinsed with deionized water three times, and air dried. Colonies were counted to calculate the number of colonies per 106 cells plated.

Isolation and purification of DNA

DNA was isolated from a part of each tissue. The remaining piece of the sample was cryopreserved and stored in −70° C. freezer. DNA was isolated by placing samples in Phosphate Buffered Saline (PBS), adding proteinase K solution, and incubating at 55° C. for 3 hrs, or until the tissue has dissolved. The samples were subsequently treated with RNase at 37° C. for 60 min. The samples were cooled to room temperature and the protein was precipitated. The samples were centrifuged and the aqueous phase was gently collected in 100% isopropanol. The samples were mixed and centrifuged and the pellet was washed in 70% ethanol. The tubes were centrifuged and the supernatant was drained off and the pellets were allowed to dry for approximately 1 to 6 hrs. The DNA was allowed to hydrate overnight at room temperature and was subsequently stored at 4° C.

Peripheral blood and bone marrow samples were first lysed with RBC lysis solution (Ammonium Chloride Buffer). DNA was then isolated from the lysates as described above. DNA was quantified by the addition of 998 $\mu$l deionized $H_2O$ and 2 $\mu$l DNA from the sample into a cuvette and vortexed. A spectrophotometer was used to determine the optical density (OD). The OD was read at 260 and 280, and the concentration of DNA was calculated for $\mu$g/ml. The DNA concentration was adjusted to 1 $\mu$g/ml using deionized water.

Anti-EGFP DNA PCR Elisa

The anti-EGFP DNA PCR Elisa assay used in these studies detects infused cMSCs utilizing oligonucleotide primers specific for GFP. For analysis of gene expression, we utilized PCR-ELISA (DIG labeling/detection) kit (Boehringer Mannheim). Briefly, PCR was performed in the presence of digoxigenin-labeled nucleotides to label the amplified product. Next, 25 $\mu$l of the PCR product was denatured and allowed to hybridize in solution to 5'-biotinylated oligonucleotide probe at 37° C. in streptavidin-coated microtiter plate. The bound probe-PCR product was detected by an anti-digoxigenin peroxidase conjugate and by use of the colorimetric substrate 2,2'Azinobis (3-ethylbenzthiazoline-sulfonic Acid) (ABTS). Titration standard curves were generated using transfected control cMSC to approximate concentration of DNA per quantity of DNA used in the assay. By first correlating with an internal standard for PCR of the DLA Class II genomic DNA, and then correlating DNA concentration to cell equivalents, and assuming one retrovirus integration event per transduced cell, an estimation of cell number can be obtained.

Quantitative measurements of DNA for GFP were noted in all bone marrow scoops/biopsies.

Post-transplant blood cell recovery

The mean day to a threshold (to 3 consecutive values) of platelets to 10,000/mm$^3$ was 12.8 (range 11–17), to 50,000/mm$^3$ was 19.8 (range 16–25), and to 100,000/mm$^3$ 23.0 (range 20–27). The mean day to a threshold value (to 3 consecutive days) of absolute neutrophil cells to 500/mm$^3$ was 9.3 (range 8–11), and to 1,000/mm$^3$ was 10.5 (range 9–13).

Interim bone marrow aspirates

When platelets recovered consistently to values greater than 50,000 per $mm^3$, an interim bone marrow aspirate was collected from the iliac crest. This procedure was performed on day 27 in study for CAN-07-01 and CAN-07-02, and on day 29 for CAN-07-03 and CAN-07-04.

RESULTS

Upon histopathological evaluation of all tissues from CAN-07-01 and CAN-07-02, euthanised on day 43, findings were negative for ectopic connective tissue and for subacute GVHD.

Detectable DNA signal could be found within 1 hour of infusion and again at 2 days. One sample could be quantitatively measured at 3 days post infusion for GFP DNA. This timepoint is consistent with the previous observations in the autologous canine transplant study in which signal was found at 2 and 3 days.

Day 100 necropsy data in CAN-07-03 and CAN-07-04 for GFP+ cells showed GFP signal (1 GFP+ cell equivalent per 10 micrograms PCR input DNA) in the femur and humerus of CAN-07-03 and in the humerus of CAN-07-04.

In this model it was possible to detect skin graft-versus-host-disease (GVHD) by observing the redness of the eyes and ears of the animals. Using this indicator, it was determined that the animals that received mesenchymal stem cells had a lower incidence of and/or lower severity of GVDH compared to the control animals that were not treated with mesenchymal stem cells.

These results demonstrate that allogeneic MSCs can support the rapid engraftment of bone marrow hematopoietic cells. No transfusion support was needed. There was no clinical evidence of GvHD. Platelet recovery was faster than in historical controls. There was evidence of chimerism in stromal cells after allogeneic transplantation. The option to engraft allogeneic tissue by using allogeneic MSCs broadens the range of transplant material usable in clinical transplant scenarios.

What is claimed is:

1. A process for treating a transplant recipient to reduce in said recipient an immune response of effector cells against an alloantigen to the effector cells, comprising;
    administering to a transplant recipient mesenchymal stem cells in an amount effective to reduce an immune response of effector cells against an alloantigen to the effector cells, whereby in the transplant recipient the effector cells have a reduced immune response against the alloantigen.

2. The process of claim 1 wherein said effector cells are T cells.

3. The process of claim 2 wherein the T cells are from the donor and the alloantigen is from the recipient.

4. The process of claim 2 wherein the T cells are from the recipient and the alloantigen is from the donor.

5. The process of claim 2 wherein said T cells are present in a transplant.

6. The process of claim 2 wherein said MSCs are administered to a transplant recipient suffering from graft-versus-host disease.

7. The process of claim 2 wherein prior to said administration said mesenchymal stem cells (MSCs) have been expanded in culture.

8. The process of claim 2 wherein said effector cells are T cells previously activated and said immune response is the reactivation of said T cells.

9. The process of claim 2 wherein the transplant is skin.

10. The process of claim 2 wherein the mesenchymal stem cells are administered to the transplant recipient to treat rejection of the transplant by the recipient.

11. The process of claim 2 wherein the mesenchymal stem cells are human mesenchymal stem cells.

12. The process of claim 2 further comprising administering to the recipient immunosuppressive agents.

13. The process of claim 2 wherein the transplant is a solid organ.

14. The process of claim 2 wherein the solid organ is selected from heart, pancreas, kidney, lung or liver.

15. The process of claim 2 wherein said mesenchymal stem cells are administered prior to said transplant.

16. The process of claim 2 wherein said mesenchymal stem cells are administered concurrently with said transplant.

17. The process of claim 2 wherein said mesenchymal stem cells are administered as part of the transplant.

18. The process of claim 2 wherein the mesenchymal stem cells are administered subsequent to transplant.

19. The process of claim 2 wherein said mesenchymal stem cells are administered intravenously to the recipient.

20. The process of claim 2 wherein said effector cells are cells of a recipient of said donor transplant.

21. A process for treating a transplant recipient to reduce in said recipient an immune response of effector cells against an alloantigen to the effector cells, comprising:
    transplanting to a transplant recipient a transplant treated with mesenchymal stem cells in an amount effective to reduce an immune response of effector cells against an alloantigen to the effector cells, whereby in the transplant recipient the effector cells have a reduced immune response against the alloantigen.

22. The process of claim 21 wherein said effector cells are T cells.

* * * * *

UNITED STATES PATENT AND TRADEMARK OFFICE
CERTIFICATE OF CORRECTION

PATENT NO. : 6,328,960 B1
DATED : December 11, 2001
INVENTOR(S) : Kevin R. McIntosh It is certified that error appears in the above-identified patent and that said Letters Patent is hereby corrected as shown below:

Column 12,
Line 67, should begin a new paragraph starting "Needle..."

Column 16,
Line 48, delete letter "I" and replace with numeral -- 1 --

Column 17,
Line 59, delete "3 T3" and replace with -- 3T3 --

Column 20,
Line 37, delete "4 day" and replace with -- 4-day --

Column 22,
Line 8, delete "106" and replace with -- $10^6$ --

Signed and Sealed this

Twenty-seventh Day of May, 2003

JAMES E. ROGAN
*Director of the United States Patent and Trademark Office*